(12) United States Patent
Andres Garcia et al.

(10) Patent No.: US 8,008,015 B2
(45) Date of Patent: Aug. 30, 2011

(54) GENETIC MARKERS OF THE RISK OF DEVELOPING RESTENOSIS

(75) Inventors: Vicente Andres Garcia, Valencia (ES); Carlos Silvestre Roig, Valencia (ES); Patricia Fernandez Ferri, Valencia (ES); Pedro Luis Sanchez Fernandez, Madrid (ES); Francisco Fernandez Aviles, Madrid (ES); Felipe Javier Chaves Martinez, Valencia (ES)

(73) Assignee: Fina Biotech, S.L.U., Madrid (ES)

( * ) Notice: Subject to any disclaimer, the term of this patent is extended or adjusted under 35 U.S.C. 154(b) by 22 days.

(21) Appl. No.: 12/392,054

(22) Filed: Feb. 24, 2009

(65) Prior Publication Data
US 2010/0216124 A1 Aug. 26, 2010

(51) Int. Cl.
C12Q 1/68 (2006.01)
C07H 21/04 (2006.01)
(52) U.S. Cl. .......................... 435/6; 536/24.3; 536/23.1
(58) Field of Classification Search .................. None
See application file for complete search history.

(56) References Cited

OTHER PUBLICATIONS

Juppner, H. Functional Properties of the PTH/PTHrP receptor. Bone 1995 vol. 17 No. 2 pp. 39S-42S.*
Pines, Jonathon et al. The differential localization of human cyclins A and B is due to a cytoplasmic retention signal in cyclin B. The EMBO Journal. 1994. vol. 13 No. 16 pp. 3772-3781.*
Andres, Vicente, "Control of vascular cell proliferation and migration by cyclin-dependent kinase signaling: new perspectives and therapeutic potential" *Cardiovascular Res.* (2004) 63: 11-21.
Baz, et al., "Spanish Cardiac Catheterization and Coronary Intervention Registry. 17th Official Report of the Spanish Society of Cardiology Working Group on Cardiac Catheterization and Interventional Cardiology (1990-2007)" *Rev. Esp. Cardiol.* (2008) 61(12): 1298-1314 (English Abstract Only).
Cogswell, et al., "Human cycline B1 gene, promoter region" Access No. U22364 in the GenBank database, May 16, 1995.
Costa, Marco A. and Daniel I. Simon, "Molecular Basis of Restenosis and Drug-Eluting Stent" *Circulation* (2005) 111: 2257-2273.
Dunham, et al., "*Homo sapiens* chromosome 13, GRCh37 primary reference assembly" Access No. NC_000013 in the GenBank database, Jun. 10, 2009.
Dzau, et al., "Vascular proliferation and atherosclerosis: New perspectives and therapeutic strategies" *Nature Medicine* (2002) 8(11): 1249-1256.

Ekholm, Susanna V. and Steven I. Reed, "Regulation of $G_1$ cyclin-dependent kinases in the mammalian cell cycle" *Current Opinion in Cell Biol.* (2000) 12: 676-684.
Farina, et al., "Down-regulation of cyclin B1 gene transcription in terminally differentiated skeletal muscle cells is associated with loss of functional CCAAT-binding NG-Y complex" *Oncogene* (1999) 18: 2818-2827.
Lazaro y de Mercado, Pablo, "Drug-Eluting Stents: Efficacy, Effectiveness, Efficiency and Evidence" *Rev. Esp. Cardiol.* (2004) 57(7): 608-612.
Massague, Joan, "G1 cell-cycle control and cancer" *Nature* (2004) 432: 298-306.
Monraats, et al., "Genetic Inflammatory Factors Predict Restenosis After Percutaneous Coronary Interventions" *Circulation* (2005) 112: 2417-2425.
Monraats, et al., "Inflammation and apoptosis genes and the risk of restenosis after percutaneous coronary intervention" *Pharmacogentics and Genomics* (2006) 16: 757-754.
Monraats, et al., "Interleukin 10: a new risk marker for the development of restenosis after percutaneous coronary intervention" *Genes and Immunity* (2007) 8: 44-50.
Morishita, et al., "Pharmacokinetics of antisense oligodeoxyribonucleotides (cyclin $B_1$ and CDC 2 kinase) in the vessel wall in vivo: enhanced therapeutic utility for restenosis by HVJ-liposome delivery" *Gene* (1994) 149: 13-19.
Nabel, Elizabeth G., "CDKS and CKIS: Molecular Targets for Tissue Remodelling" *Nat. Rev. Drug Discovery* (2002) 1: 587-598.
Rieder, et al., "*Homo sapiens* cyclin-dependent kinase inhibitor 1A (p21, Cip1) (CDKN1A) gene, compete cds" Access No. AF497972 in the GenBank database, Apr. 11, 2002.
Rudez, et al., "Platelet Receptor P2RY12 Haplotypes Predict Restenosis After Percutaneous Coronary Interventions" *Human Mutation* (2008) 29(3): 375-380.
Santamaria, David, and Sagrario Ortega, "Cyclins and CDKS in development and cancer: lessons form genetically modified mice" *Frontiers in Bioscience* (2006) 11: 1164-1188.
Schmutz, et al., "*Homo sapiens* chromosome 5, GRCh37 primary reference assembly" Access No. NC_000005 in the GenBank database, Jun. 10, 2009.
Sciortino, et al., "The *cyclin B1* gene is actively transcribed during mitosis in HeLa cells" *EMBO Reports* (2001) 2(11): 1018-1023.
Serruys, et al., "Coronary-Artery Stents" *N. Engl. J. Med.* (2006) 354: 483-495.
Shaulian, Eitan and Michael Karin, "AP-1 in cell proliferation and survival" *Oncogene* (2001) 20: 2390-2400.
Wessely, et al., "Sirolimus and Paclitaxel on Polymer-Based Drug-Eluting Stents: Similar but Different" *J. Am. College of Cardiology* (2006) 47(4): 708-714.

* cited by examiner

*Primary Examiner* — Amanda Shaw
(74) *Attorney, Agent, or Firm* — Knobbe Martens Olson & Bear LLP

(57) ABSTRACT

Methods and kits for diagnosing the risk of developing restenosis after revascularization by implantation of stents based on the detection of single-nucleotide polymorphisms (SNPs).

5 Claims, 23 Drawing Sheets

| Gene (protein) | Polymorphism GenBank Access number | Position | Localization |
|---|---|---|---|
| CCNA1 (Cyclin A1) | rs3814805 | -1917C→G | Promoter region |
| | rs3814803 | -1669 C→T | Promoter region |
| | rs7985423 | -170C→G | Promoter region |
| | rs7998324 | +3910C→T | Intronic region |
| | rs2282411 | +7733(G)C→T | Intronic region |
| CCNE1 (Cyclin E1) | rs7257330 | -1078A→G | Promoter region |
| | rs3218026 | +237A→C | Intronic region |
| | rs3218027 | +451C→T | Intronic region |
| | rs3218028 | +484 -→G | Intronic region |
| | rs3218068 | +10443C→T | Intronic region |
| | rs1406 | +12211G→T | UTR 3' region |
| CCNB1 (Cyclin B1) | rs8192258 | -1055-→A | Promoter region |
| | rs350099 | -957C→T | Promoter region |
| | rs352626 | -710C→T | Promoter region |
| | rs350104 | -475C→T | Promoter region |
| | rs2069429 | -160A→G | Promoter region |
| | rs164390 | +102G→T | 5' untraslated region |
| | rs875459 | +7010G→T | Intronic region |
| | rs1128761 | +8334A→G | Exon |
| CCND1 (Cyclin D1) | rs1944129 | -1938A→G | Promoter region |
| | rs3212860 | -766A→T | Promoter region |
| | rs3862792 | +6983C→T | Exon |
| | rs603965 | +7037A→G | Exon |
| | rs3212892 | +9987A→G | Intronic region |
| | rs7177 | +10242A→C | UTR 3' region |

FIG. 1

| Gene (protein) | Polymorphism GenBank Access number | Position | Localization |
|---|---|---|---|
| CDKN1A (p21 Kip1/Cip1) | rs3829963 | -2101A→C | Promoter region |
| | rs733590 | -1284C→T | Promoter region |
| | rs762623 | -1021A→G | Promoter region |
| | rs3176337 | +2433A→C | Intronic region |
| | rs3176345 | +4078C→G | Intronic region |
| | rs3176352 | +5852C→G | Intronic region |
| | rs3176356 | +6990C→T | Intronic region |
| | rs1059234 | +7110C→T | UTR 3' region |
| | rs3176358 | +7475A→G | UTR 3' region |
| CDKN1B (p27 Kip1/Cip1) | rs3759217 | -1857C→T | Promoter region |
| | rs34330 | +386C→T | UTR 5' region |
| | rs2066827 | +790G→T | Exon |
| | rs34329 | +2924C→G | Intronic region |
| CDKN1C (p57 Kip1/Cip1) | rs3741341 | +1147C→T | Exon |
| | rs452338 | +378174G→T | Region 5' close to gene |
| | rs431222 | +378378C→T | Region 5' close to gene |
| | rs928656 | *A→G | - |
| | rs450563 | *A→G | - |
| TP53 (p53) | rs1042522 | +7958C→G | Exon |
| | rs17883323 | +8105A→C | Intronic region |
| | rs17551157 | +7233-→C | Intronic region |
| | rs2287498 | +21046A→G | Exon |

FIG. 2

| Gene (protein) | Polymorphism | GenBank Access number | Localization |
|---|---|---|---|
| CCNB1 (Cyclin B1) | SNP1 : -957C→T | rs350099 | Promoter region |
| | SNP2 : -475C→T | rs350104 | Promoter region |
| | SNP3 +102G→T | rs164390 | 5' untranslated region |
| | SNP4 : +7010G→T | rs875459 | Intronic region |
| CCNA1 (Cyclin B1) | SNP5 : +7733(G)C→T | rs2282411 | Intronic region |
| CDKN1A (p21$^{Kip1/Cip1}$) | SNP6 : -1284C→T | rs733590 | Promoter region |

FIG. 3

| Gene | Chromosome locus | Polymorphism | Genetic model | | P | Ratio of Odd | 95% IC |
|---|---|---|---|---|---|---|---|
| CCNB1 | 5q12 | SNP1: -957C→T rs350099 | Dominance | TT | 0.028 | 1.74 (TT with respect to CC+TC) | 1.06-2.63 |
| | | | | CC + TC | | | |
| | | SNP2: -475C→T rs350104 | Dominance | CC | 0.038 | 1.77 (CC with respect to TT+TC) | 1.03-3.04 |
| | | | | TT + TC | | | |
| | | SNP3: +102G→T rs164390 | Dominance | GG | 0.016 | 1.81 (GG with respect to TT+GT) | 1.12-2.94 |
| | | | | TT + GT | | | |
| | | SNP4: +7010G→T rs8754459 | Dominance | GG | 0.033 | 1.78 (GG with respect to TT+GT) | 1.04-3.03 |
| | | | | TT + GT | | | |
| | | | Codominance | TT | 0.019 | 1.26 (TT with respect to CC) | 0.31-5.03 |
| | | | | CC | | | |
| CCNA1 | 13q12.3-q13 | SNP5: +7733(G)C→T rs2282411 | | CT | 0.019 | 3.10 (CT with respect to CC) | 1.37-7.00 |
| | | | | GG | | | |
| | | | Dominance | GT + TT | 0.019 | 1.78 (GG with respect to TT+GT) | 1.04-3.03 |
| | | | | TT | | | |
| | | | Codominance | CT | 0.035 | 1.92 (TT with respect to CT) | 1.03-3.57 |
| | | | | CC | | | |
| CDKN1A | 6p21.1 | SNP6: -1284C→T rs733590 | | TT | | 2.38 (TT with respect to CC) | 1.12-5.00 |
| | | | Dominance | | 0.012 | 2.08 (TT with respect to CC+CT) | 1.17-3.70 |
| | | | | CC +CT | | | |

FIG. 4

| Probe | Sequence | Description |
|---|---|---|
| SNP1-T (SEQ ID NO 19 & 20)) | 5'-GAGTCTCTATTTGGCTCTTATACC-3'<br>3'-CTCAGAGATAAACCGAGAATATGG-5' | Sequence carrying T allele of the SNP rs350099 |
| SNP1-C (SEQ ID NO 21 & 22) | 5'-GAGTCTCTATC GGCTCTTATACC-3'<br>3'-CTCAGAGATA G CCGAGAATATGG-5' | Sequence carrying C allele of the SNP rs350099 |
| NF-Ycons (SEQ ID NO 23 & 24) | 5'-CCGCAGCCGCCAATGGGAAGGGAGTGA-3'<br>3'-GGCGTCGGCGGTTACCCTTCCCTCACT-5' | Sequence carrying a NF-Y consensus binding site |
| NF-Ymut (SEQ ID NO 25 & 26) | 5'-CCGCAGCCGTTAATGGGAAGGGAGTGA-3'<br>3'-GGCGTCGGCAATTACCCTTCCCTCACT-5' | Sequence carrying a mutated NF-Y binding site (CC→TT) |
| SNP2-T (SEQ ID NO 27 & 28) | 5'-TAATGTGTGAT CCTGGCAAAG-3'<br>3'-ATTACACACTA GGACCGTTTC-5' | Sequence carrying T allele of the SNP rs350104 |
| SNP2-C (SEQ ID NO 29 & 30) | 5'-TAATGTGTGACCCTGGCAAAG-3'<br>3'-ATTACACACTGGGACCGTTTC-5' | Sequence carrying C allele of the SNP rs350104 |
| AP-1cons (SEQ ID NO 31 & 32) | 5'-CGCTTGATGAGTCAGCCGGAA-3'<br>3'-GCGAACTACTCAGTCGGCCTT-5' | Sequence carrying an AP-1 consensus binding site |
| NF-Y (-30/-10) (SEQ ID NO 33 & 34) | 5'-GGCAGCCGCCAATGGGAAGG-3'<br>3'-CCGTCGGCGGTTACCCTTCC-5' | Sequence carrying a NF-Y binding site of the human CCNB1 gene promoter |

FIG. 6

Seq. No.1

TGACTTCCAGCGCCAGGAGTCTCTAT (C/T)GGCTCTTATACCGTTGCTCTATGGG

Seq. No.2

TCAGTTCCCCCGTTGCTAATGTGTGA (C/T)CCTGGCAAAGTCATCTAAGTCGCTG

Seq. No.3

GCGGAACGGCTGTTGGTTTCTGCTGG(G/T)TGTAGGTCCTTGGCTGGTCGGGCCT

Seq. No.4

CATGTTTGCTTTATTTCTTGGTGATG (G/T)TGTTGTTTGTGGTTGACCATATGAA

Seq. No.5

GGATGATTGGGAAAGGTTGATTTTTA (C/T)GCTCCTTGGCACTGGAAGTTCCTAG

Seq. No.6

CTGCTCCAAGCCTGGGTTCTGTTTTT(C/T)AGTGGGATTTCTGTTCAGATGAACA

FIG. 11

GENETIC MARKERS OF THE RISK OF DEVELOPING RESTENOSIS

REFERENCE TO SEQUENCE LISTING

The present application is being filed along with a Sequence Listing in electronic format. The Sequence Listing is provided as a file entitled HERR41001AUS.TXT, created Feb. 24, 2009, which is 7.9 KB in size. The information in the electronic format of the Sequence Listing is incorporated herein by reference in its entierety.

FIELD OF THE INVENTION

The present invention has its application within the healthcare sector, in the field of Molecular Biotechnology. In particular, this invention is aimed at a method for diagnosing the risk of developing restenosis after revascularization by implantation of stents based on the detection of single-nucleotide polymorphisms (SNPs).

BACKGROUND OF THE INVENTION

The clinical treatment most frequently used for the revascularization of vessels affected by arteriosclerosis is transluminal percutaneous coronary angioplasty (PCTA). A pathological process frequently associated to this intervention is restenosis, consisting of the excessive reocclusion of the operated vessel. Restenosis has a high healthcare and socioeconomic impact, since it makes it necessary to repeat the PCTA or subjecting the patient affected to alternative revascularization therapies (for example, aortocoronary by-pass). In comparison with the native atheromatous lesion, characterized by a slow development (typically over decades), the restenotic lesion usually grows during the first 4-12 months after the PCTA (Serruys, Kutryk and Ong, *"Coronary-artery stents"*, N Engl J Med 2006, 354, 483-95). Currently, over 90% of PCTA use support metal endoprostheses called stents which increase the safety of the procedure and have reduced restenosis rates to 15-30%, compared with rates of 25-50% typically associated to conventional PCTA (Serruys, Kutryk and Ong, *"Coronary-artery stents"*, N Engl J Med 2006, 354, 483-95, Andrés, *"Control of vascular cell proliferation and migration by cyclin-dependent kinase signalling: new perspectives and therapeutic potential"*, Cardiovasc Res 2004, 63, 11-21). Restenosis rates are further reduced with the use of drug-eluting stents.

Restenosis is a multifactorial process in which various cell types intervene, mainly platelets, monocytes/macrophages, endothelial cells (ECs), and smooth muscle cells (SMCs). It is accepted that the growth of the restenotic lesion, also called neointimal lesion, is a process started by the mechanical damage that causes the implantation of the stent (Andrés, *"Control of vascular cell proliferation and migration by cyclin-dependent kinase signalling: new perspectives and therapeutic potential"* Cardiovasc Res 2004, 63, 11-21, Costa and Simon, *"Molecular basis of restenosis and drug-eluting stents"*, Circulation 2005, 111, 2257-73). The initial acute phase of restenosis involves the activation of platelets and localized thrombosis, accompanied by the recruitment of circulating monocytes, neutrophils and lymphocytes on the damaged arterial surface. These cell types unleash a chronic inflammatory response characterized by the activation of the SMCs resident in the tunica media, which adopt a "synthetic" phenotype characterized by morphological changes, expression of embryonic isoform of contractile proteins, high responsiveness to growth and chemotactic stimulus, and abundant synthesis of extracellular matrix. A plethora of chemotactic and mitogenic factors produced by the cells of the neointimal lesion causes a first proliferative phase of the SMCs of the tunica media and their migration towards the lesion, followed by a second hyperplastic response of the SMCs of the neointimal lesion (Andrés, *"Control of vascular cell proliferation and migration by cyclin-dependent kinase signalling: new perspectives and therapeutic potential"*, Cardiovasc Res 2004, 63, 11-21, Costa and Simon, *"Molecular basis of restenosis and drug-eluting stents"* Circulation 2005, 111, 2257-73). The resolution of the inflammation and cicatrization of the vascular lesion in later stages of the PCTA goes accompanied by the restoration of the contractile phenotype of neointimal SMCs and changes in the composition of the extracellular matrix which becomes more similar to the undamaged arterial wall. As previously indicated, if the restenosis is excessive, the clinical symptoms reappear making a further revascularization intervention necessary.

Among the neointimal hyperplasia regulators identified in animal and human studies, the following are included: thrombogenic factors (for example, tissue factor, thrombin receptor), cell adhesion molecules (for example, VCAM, ICAM, LFA-1, Mac-1), signal transducers (for example, PI3K, MEK/ERK), transcription factors (for example, NF-κB, E2F, AP-1, c-myc, c-myb, YY1, Gax), cell cycle regulatory proteins (for example, pRb, p21, p27, CDK2, CDC2, cyclin B1, PCNA), growth factors (for example, PDGF-BB, TGFβ, FGF, IGF, EGF, VEGF), inflammatory cytokines (for example, TNFα), chemotactic factors (for example, CCR2, MCP-1), and metalloproteases (for example, MMP-2, MMP-9).

The essentially hyperproliferat ive character of restenosis has generated great interest in the study of the role that cell cycle regulatory genes may play in this pathological process. In mammals, the cell cycle is regulated positively by holoenzymes composed of a catalytic subunit called cyclin-dependent kinase (CDK) and a regulatory subunit called cyclin (Ekholm and Reed, *"Regulation of G(1) cyclin-dependent kinases in the mammalian cell cycle"*, Curr Opin Cell Biol 2000, 12, 676-84). The sequential activation of the CDK/cyclins permits different events of phosphorylation of cell substrates involved in cell proliferation. On the other hand, there are inhibitory proteins of CDKs/cyclins called CKIs (CDK inhibitors), which are subdivided into the CIP/KIP (p21, p27 and p57) and INK4 (p15, p16, p18, and p19) subfamilies. The accumulation of CKIs in response to anti-mitogenic stimuli provokes the reversible inhibition of CDK/cyclin complexes. Expression studies and gene therapy experiments have revealed the importance of these molecules in the development of the neointimal lesion. Thus, the analysis of obstructive vascular lesions induced by mechanical damage in animal and human models of angioplasty has demonstrated alterations in the expression of cell cycle regulatory genes (for example, CDKs, cyclins, CKIs, p53, pRb), and numerous experimental animal studies have shown that the inactivation of CDKs and cyclins (for example, cyclin B, CDK2, CDK1), or the overexpression of growth suppressors (for example p21, p27, pRb, p53) inhibits the development of obstructive vascular lesions after angioplasty (Andrés, *"Control of vascular cell proliferation and migration by cyclin-dependent kinase signalling: new perspectives and therapeutic potential"*, Cardiovasc Res 2004, 63, 11-21, Nabel, *"CDKs and CKIs: molecular targets for tissue remodelling"* Nat Rev Drug Discov 2002, 1, 587-98, Dzau, Braun-Dullaeus and Sedding, *"Vascular proliferation and atherosclerosis: new perspectives and therapeutic strategies"*, Nat Med 2002, 8, 1249-56).

Numerous systemic therapeutic approaches to prevent or treat restenosis failed in clinical trials despite encouraging preclinical data derived from various animal models. However, the recent introduction of the antiproliferative drug-eluting stents (DES) has revolutionized interventional cardiology. We should highlight the use of stents to deliver sirolimus (also called rapamycin or rapamune) and paclitaxel (also called taxol), two lipophilic drugs which have as target the common final route of cell proliferation, the mitotic cycle of the eukaryotic cell. The use of these devices, which locally release high doses of the drug in the damaged arterial wall, has significantly reduced restenosis rates (Costa and Simon, "*Molecular basis of restenosis and drug-eluting stents*", Circulation 2005, 111, 2257-73, Wessely, Schomig and Kastrati, "*Sirolimus and Paclitaxel on polymer-based drug-eluting stents: similar but different*", J Am Coll Cardiol 2006, 47, 708-14). For this reason, 2 DESs are implanted out of every 3 stents currently implanted in Europe (Baz, Mauri, Albarran and Pinar, "*[Spanish Cardiac Catheterization and Coronary Intervention Registry. 16th Official Report of the Spanish Society of Cardiology Working Group on Cardiac Catheterization and Interventional Cardiology (1990-2006)]*", Rev Esp Cardiol 2007, 60, 1273-89). Relevant drawbacks of the use of DES with respect to conventional stents are their high cost (2-3 times more) and the need to prolong the anti-platelet treatment to avoid adverse events associated to late thrombosis (reviewed in Lazaro and de Mercado, "*Stents recubiertos de fármacos: eficacia, efectividad, eficiencia y evidencia*", Revista Española de Cardiología 2004, 57, 608-12).

Due to the high healthcare and socio-economic impact of restenosis, it would be highly useful to have biomarkers that could be quantified in a reproducible, reliable and cost effective form in patients needing revascularization. The possibility of estimating the risk of restenosis in these patients could help in taking therapeutic decisions, for example, implantation of stents versus aortocoronary by-pass, or use of conventional stents versus DES (more expensive and with an increased risk of late thrombosis).

Single-nucleotide polymorphisms (SNP) are genetic variants present by millions throughout the human genome. In recent years SNPs have been identified in human genes which are associated with a greater or lesser risk of developing restenosis, including the gene of the beta2-adrenergic receptor, CD14, colony stimulating factor (CSF), eotaxin, caspase-1, P2RY12 receptor, and interleukin-10 (Monraats et al. "*Inflammation and apoptosis genes and the risk of restenosis after percutaneous coronary intervention*", Pharmacogenet Genomics 2006, 16, 747-754; Monraats et al. "*Interleukin 10: a new risk marker for the development of restenosis after percutaneous coronary intervention*", Genes Immun 2007, 8, 44-50; Monraats et al. "*Genetic inflammatory factors predict restenosis after percutaneous coronary interventions*", Circulation 2005, 112, 2417-25; Rudez et al. "*Platelet receptor P2RY12 haplotypes predict restenosis after percutaneous coronary interventions*", Hum Mutat 2008, 29, 375-80).

However, no genotype-phenotype associations have been described to date relating SNPs in cell cycle regulatory genes with a greater or lesser risk of developing restenosis.

The authors of the present invention, after important research work, have identified different SNPs in various cell cycle regulatory genes with potential diagnostic value as genetic risk markers for developing restenosis. Specifically, they have identified the SNPs rs164390, rs350099, rs350104, rs875459, in the CCNB1 gene (cyclin B1 protein); rs2282411, in the CCNA1 gene (cyclin A1 protein) and rs733590, in the CDKN1A gene (p21Kip1/Cip1 protein) as markers of the diagnosis of the risk of developing restenosis.

These markers constitute a very important advance in the taking of therapeutic decisions. For example, patients with relative low risk of developing restenosis could receive a conventional stent, whilst the use of DES (more expensive and with a greater risk of late thrombosis) could be limited to patients with greater risk.

Based on these findings, the authors of the invention have developed a method to determine the risk of restenosis after the implantation of a stent based on the detection of these 6 SNPs as diagnostic markers of said risk. Likewise, they have developed a kit to carry out said diagnosis.

BRIEF DESCRIPTION OF THE FIGURES

FIG. 1: Table summarizing 25 polymorphisms examined in cyclin genes.

FIG. 2: Table summarizing 22 polymorphisms examined in cell growth suppressor genes.

FIG. 3: Table summarizing 6 SNPs associated in a statistically significant manner with the risk of developing restenosis after the implantation of a stent.

FIG. 4: Table summarizing the results of the logistic regression analysis of the SNPs associated with risk of developing restenosis after the implantation of a stent. The analysis was performed using the SNPStat software

FIG. 6: List of probes used in the Electrophoretic Mobility Shift Assay (EMSA).

FIG. 11: Sequences of nucleotides adjacent to the 6 SNPs which show statistically significant association with risk of developing restenosis after the implantation of a stent.

OBJECT OF THE INVENTION

Figure 5:
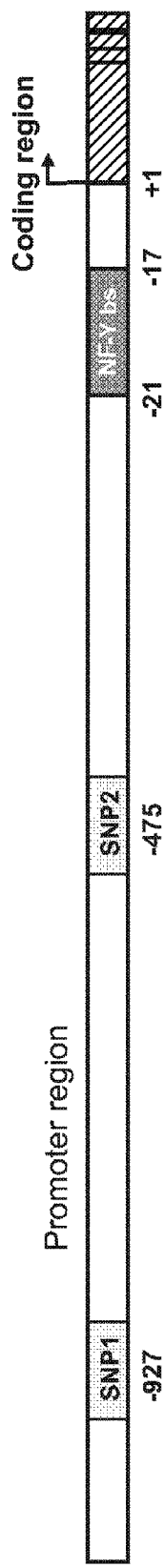
FIG. 5: Diagram of the promoter region of the human CCNB1 gene showing the localization of the SNPs rs350099 (SNP1) and rs350104 (SNP2), and the binding site for the transcription factor NF-Y (NF-Y bs).

The object of the invention is a method for determining the risk of an individual of developing restenosis after the implantation of a stent based on the analysis of a sample to determine the genotype in at least one single-nucleotide polymorphism (SNP) selected from rs350099, rs350104, rs164390 and rs875459, in the CCNB1 gene, and, optionally of rs2282411 and/or rs733590, in the CCNA1 and CDKN1A genes, respectively, where the presence of specific alleles in any of these polymorphisms, as indicated below, is indicative of the risk of developing restenosis.

A kit to carry out said method which comprises a set of probes and reagents suitable for determining the genotype of the cited polymorphisms is also an object of the invention.

Finally an object of the invention is the use of one or more of the cited polymorphisms, rs350099, rs350104, rs164390, rs875459 and, optionally, rs2282411 and rs733590, as markers of the risk of an individual of developing restenosis after the implantation of a stent.

DESCRIPTION OF THE INVENTION

A main aspect of the invention contemplates a method for determining the risk of an individual of developing restenosis after the implantation of a stent which comprises: a) obtaining genomic DNA from a sample of the individual; b) analysing the DNA of the sample to determine the genotype of at least one single-nucleotide polymorphism (SNP) in the CCNB1 gene, selected from rs350099 (SNP1), rs350104 (SNP2), rs164390 (SNP3) and rs875459 (SNP4), as defined in FIG. 3, where the presence of specific alleles in any of these polymorphisms, as defined below, is indicative of the risk of developing restenosis (See FIG. 4).

In a preferred embodiment, step b) comprises analysing the DNA of the sample to determine the combination of genotypes of the polymorphisms SNP1 and SNP2.

Polymorphism rs350099 (SNP1) (See FIG. 3), is localized in the promoter region, −957 from the start of the transcription of the CCNB1 gene, which encodes for the cyclin B1 protein, a positive regulator essential for cell proliferation in various physiopathological contexts (Santamaria and Ortega, "Cyclins and CDKS in development and cancer: lessons from genetically modified mice" Front Biosci 2006, 11, 1164-88), including the development of the neointimal lesion induced by mechanical vascular damage (Morishita, Gibbons, Kaneda, Ogihara and Dzau, "Pharmacokinetics of antisense oligodeoxyribonucleotides (cyclin B1 and CDC 2 kinase) in the vessel wall in vivo: enhanced therapeutic utility for restenosis by HVJ-liposome delivery" Gene 1994, 149, 13-9). Position −957 also corresponds to the base in position 36 of the sequence of 1172 base pairs (bp) of the CCNB1 gene (access number U22364 in the GenBank database). Its use as diagnostic marker of risk of developing restenosis after implantation of stents in a human being is determined by the detection of the T allele in homozygosis (T/T genotype) of this SNP (See FIG. 4). Furthermore, the authors of the present invention, in the sequence with the T allele, have identified a sequence (CCAAT) which constitutes a specific binding site for the transcription factor NF-Y (See FIGS. 7-9).

The transcription factor NF-Y, through its binding to two cis-regulatory sequences localized in region −150 to +182 of the human gene promoter CCNB1, is essential for its transcriptional activation in cells with high proliferative rate (Sciortino, Gurtner, Manni, Fontemaggi, Dey, Sacchi, Ozato and Piaggio, "The cyclin B1 gene is actively transcribed during mitosis in HeLa cells", EMBO Rep 2001, 2, 1018-23, Farina, Manni, Fontemaggi, Tiainen, Cenciarelli, Bellorini, Mantovani, Sacchi and Piaggio, "Down-regulation of cyclin B1 gene transcription in terminally differentiated skeletal muscle cells is associated with loss of functional CCAAT-binding NF-Y complex", Oncogene 1999, 18, 2818-27).

FIG. 5 is a diagram of the promoter region of the human CCNB1 gene showing the localization of the SNPs studied by the EMSA assay (SNP1 and SNP2). The NF-Ybs box represents the CCAAT sequence located in position −21/−17 of the promoter to which the transcription factor NF-Y binds. The start of the transcription is designated with the value +1 and it is represented with a curved arrow.

The polymorphism rs350104 (SNP2), (See FIG. 3), is localized in the promoter region, −475 from the start of the transcription of the CCNB1 gene, which encodes for the cyclin B1 protein. Position −475 also corresponds to the base in position 519 of the sequence of 1172 bp of the CCNB1 gene (Access number U22364 in the GenBank database). Its use as diagnostic marker of the risk of developing restenosis after implantation of a stent in a human being is determined by the detection of the C allele in homozygosis (C/C genotype) of this SNP (See FIG. 4). Furthermore, the authors of the invention have identified in the sequence with the C allele a binding site for the transcription factor AP-1 of greater affinity with respect to the sequence with the T allele of this polymorphism (See FIG. 10).

AP-1 is a transcription factor widely related to the regulatory processes of activation of a large quantity of cell cycle genes, including cyclins (Shaulian and Karin, "AP-1 in cell proliferation and survival", Oncogene 2001, 20, 2390-400)

The polymorphism rs164390 (SNP3), (See FIG. 3), is localized in position +102, 5' untranslated region, of the CCNB1 gene, which encodes for the cyclin Bl protein. Position +102 also corresponds to the base in position 104 of the sequence of 11160 bp of the CCNB1 gene (Access number NC_000005 in the GenBank database). Its use as diagnostic marker of the risk of developing restenosis is determined by the detection of the G allele in homozygosis (G/G genotype) of this SNP (See FIG. 4).

The Polymorphism rs875459 (SNP4), (See FIG. 3), is localized at +7010 with respect to the start of the transcription of the CCNB1 gene, which encodes for the cyclin B1 protein. Position +7010 also corresponds to the base in position 7012 of the sequence of 11160 bp of the CCNB1 gene (Access number NC_000005 in the GenBank database). Its use as diagnostic marker of the risk of developing restenosis after implantation of a stent in a human being is determined by the detection of the G allele in homozygosis (G/G genotype) of this SNP (See FIG. 4).

In a particular embodiment, step b) of the method additionally comprises determining the genotype of the polymorphism rs2282411 (SNP5), of the CCNA1 gene, as defined in FIG. 3.

The Polymorphism rs2282411 (SNP5), (See FIG. 3), is localized at +7733 with respect to the start of the transcription of the CCNA1 gene, which encodes for the protein Cyclin A1, also a positive regulator of the cell cycle (Santamaria and Ortega, "Cyclins and CDKS in development and cancer: lessons from genetically modified mice", Front Biosci 2006, 11, 1164-88). Position +7733 also corresponds to the base in position 7735 of the sequence of 10376 bp of the CCNA1 gene (Access number NC_000013 of the GenBank database). Its use as diagnostic marker of the risk of developing restenosis after implantation of stents in a human being is determined by the detection of the T allele in homozygosis or in heterozygosis (TT or CT genotypes), in a codominance model, or the detection of the G allele in homozygosis in a dominance model (GG genotype), of this SNP (See FIG. 4).

In another particular embodiment, step b) of the method additionally comprises determining the genotype of the polymorphism rs733590 (SNP6), of the gene CDKN1A, as defined in FIG. 3.

The Polymorphism rs733590 (SNP6), (See FIG. 3), is localized in the promoter region, −1284 from the start of the transcription of the CDKN1A gene, which encodes for the protein p21$^{Kip1/Cip1}$, a negative regulator of the cell cycle in various physiopathological contexts (Massague, "G1 cell-cycle control and cancer", Nature 2004, 432, 298-306), including the development of the neointimal lesion induced by mechanical vascular damage (Andrés, "Control of vascular cell proliferation and migration by cyclin-dependent kinase signalling: new perspectives and therapeutic potential", Cardiovasc Res 2004, 63, 11-21, Nabel, "CDKs and CKIs: molecular targets for tissue remodelling", Nat Rev Drug Discov 2002, 1, 587-98). Position −1284 also corresponds to the base in position 57 of the sequence of 10907 bp of the CDKN1A gene (Access number: AF497972 of the GenBank database). Its use as diagnostic marker of the risk of developing restenosis after implantation of stents in a human being, comprises the detection of the T allele in homozygosis (T/T genotype), both in dominant and codominant model, of this SNP (See FIG. 4).

FIG. 11 shows the 6 sequences of nucleotides (SEQ ID NO 1-6) adjacent to the 6 SNPs (SNP1-SNP6), according to information recorded in the public database GenBank ("National Center of Biotechnology Information", NCBI). The two polymorphic variants of each SNP are shown between brackets.

The method can be applied to DNA obtained from different samples of the patients, such as saliva, blood or leukocytes purified from blood.

The genotyping of the SNPs object of this invention is used in the development of a kit to diagnose the risk of developing restenosis after implantation of stents. The most appropriate methodologies for identifying SNPs are minisequencing (use of probes prior to the polymorphisms and extension with ddNTPs marked fluorescently to view them in an automatic sequencer); the quantitative PCR (amplification of the region where each polymorphism is found and identify them either by different types of probes or by melting curves); the PCR and digestion by restriction (use as primers in the reaction of PCR oligonucleotides modified to create restriction sites to amplify the region where the polymorphism is and digestion with the suitable restriction enzyme for its use with an automatic sequencer, agarose gels, etc.); and the allele-specific amplification and viewing in an automatic sequencer, agarose gels, etc.

Preferably, to determine these polymorphisms the methodology of melting curves by "high resolution melting curves" has been used, wherein the DNA is amplified from the region where the polymorphisms of interest are found and the melting curves are analyzed in a quantitative thermocycler. It is a simple, fast and reliable methodology, consisting of the amplification with suitable oligonucleotides from the region which contains the polymorphisms, the latter being identified by the melting curves obtained on subjecting the product obtained to a temperature ramp according to the characteristics of the system used. This makes it possible to develop the diagnostic tests in a simple and reliable manner.

Thus, in another main aspect of the invention a kit for performing the method of the invention is contemplated which comprises a set of oligonucleotides and reagents suitable for determining the genotype of a polymorphism of the CCNB1 gene, selected from SNP1, SNP2, SNP3, SNP4, and their combinations.

In a preferred embodiment, the pair of oligonucleotides (primers) used for the genotyping of the SNP1 has the sequences SEQ ID NO 7 (sense) and SEQ ID NO 8 (antisense) (See table 3).

In another preferred embodiment, the pair of oligonucleotides used for the genotyping of SNP2 has the sequences SEQ ID NO 9 (sense) and SEQ ID NO 10 (antisense) (See table 3).

In another preferred embodiment, the pair of oligonucleotides used for the genotyping of SNP3 has the sequences SEQ ID NO 11 (sense) and SEQ ID NO 12 (antisense) (See table 3).

In another preferred embodiment, the pair of oligonucleotides used for the genotyping of SNP4 has the sequences SEQ ID NO 13 (sense) and SEQ ID NO 14 (antisense) (See table 3).

Optionally, in a particular embodiment the kit can also include oligonucleotides suitable for the genotyping of SNP5, of the CCNA1 gene. Preferably, the oligonucleotides used have the sequences SEQ ID NO 15 (sense) and 16 (antisense) (See table 3).

In another particular embodiment, the kit can further include oligonucleotides suitable for the genotyping of SNP6, of the CDKN1A gene. Preferably, the oligonucleotides used have the sequences SEQ ID NO 17 (sense) and 18 (antisense) (See table 3).

Finally, another main aspect of the invention relates to the use of one or more of the polymorphisms SNP1, SNP2, SNP3, SNP4 and, optionally, SNP5 and SNP6, as defined in FIG. 3, as markers of the risk of an individual of developing restenosis after the implantation of a stent.

EXAMPLES

Description of the Cohort of Patients

Patient Population

For a 12 month period, all consecutive patients admitted to the Clinica Mediterranea (Naples, Italy) and who fulfilled the following inclusion criteria were enrolled in the study: 1) percutaneous coronary intervention (PCI) in a native coronary artery, 2) treatment of a de novo lesion, 3) implantation of a bare metal stent, and 4) availability to perform coronary angiography at 6-9 months. The local ethics committee approved the study protocol, and all patients gave written informed consent.

Of the 434 patients enrolled in the study, only 284 (65%) had the angiographic follow-up at 6-9 months. These 284 patients represent the population of patients.

Biochemical Measurements

Plasma total cholesterol, high-density lipoprotein cholesterol (HDL-C), low-density lipoprotein cholesterol (LDL-C) and triglycerides were determined with enzymatic techniques. Estimated glomerular filtration rate (eGFR) was calculated by applying the Level modified Modification of Diet in Renal Disease (MDRD) formula. Chronic kidney disease was defined as an eGFR<60 ml/min/1.73 m$^2$.

Blood Samplings

Venous blood samples were extracted from patients before PCI. All samples were collected into trisodium-citrated tubes and were immediately placed in ice. Within 1 hour of collection, blood samples were centrifuged at 4000 rpm (1400 g) for 20 minutes, plasma was harvested and stored into aliquots at −80° C. until batch analysis.

Percutaneous Coronary Angioplasty

Patients received intracoronary isosorbide dinitrate (0.1-0.3 mg) prior to initial and final angiograms to achieve maximal vasodilatation. Angiographic measurements were performed with an automated computer-based system (QCA-CMS version 3.0, MEDIS, Leiden, The Netherlands). Follow-up restenosis was analyzed by measuring minimal lumen diameter (MLD) at 6-9 months following stenting. In addition, the following variables were assessed: acute gain, defined as the MLD after the procedure minus the MLD before the procedure; late loss, defined as the MLD after the procedure minus the MLD at follow-up; and loss index, defined as the average ratio of late loss to acute gain. Restenosis was defined as a degree of stenosis ≧50% at follow-up.

Statistical Analysis

Continuous variables are represented as mean+standard deviation (SD). Differences in continuous values in the two groups (as defined by the angiographic lesion progression) were performed by the Student t test or the Mann-Whitney U test, when appropriate. Categorical variables were analyzed by chi-square test. Tests were 2-sided. Data were analyzed with SPSS for Windows, version 13.0 (SPSS Inc., Chicago, Ill.).

TABLE 1

Clinical characteristics of the patients with or without restenosis after implantation of coronary stents.

|  | No restenosis (n = 168) | With restenosis (n = 116) | P |
|---|---|---|---|
| Age | 59 ± 11 | 63 ± 9 | 0.002 |
| Male | 75.3% | 77.2% | 0.71 |
| Angina pectoris* |  |  | 0.33 |
| Class I | 20.7% | 13.6% |  |
| Class II | 61.9% | 66.2% |  |
| Class III | 17.4% | 20.2% |  |
| Diabetes mellitus | 36.4% | 35.8% | 0.85 |
| Left ventricular ejection fraction % | 56 ± 10 | 56 ± 90 | 0.81 |
| Previous myocardial infarction | 48.5% | 47.8% | 0.91 |
| Family history of coronary artery disease | 31.5% | 38.2% | 0.64 |
| Systemic hypertension | 64.6% | 57.5% | 0.15 |
| Hypercholesterolemia | 51.2% | 49.1% | 0.30 |
| Active smokers | 23.1% | 20% | 0.70 |
| Statins | 89.4% | 89.1% | 0.96 |
| eGFR (ml/min/1.73 m$^2$) | 67.5 ± 17.4 | 67.6 ± 17.6 | 0.93 |
| Plasma lipids (mg/dL) |  |  |  |
| Total cholesterol | 181 ± 43 | 163 ± 38 | <0.001 |
| LDL-cholesterol | 99 ± 34 | 89 ± 31 | 0.035 |
| HDL-cholesterol | 46 ± 12 | 46 ± 15 | 0.84 |
| Triglycerides | 147 ± 74 | 156 ± 731 | 0.84 |

*According to the classification of the Canadian Cardiovascular Society (CCS). eGFR = estimated glomerular filtration rate.

TABLE 2

Angiographic characteristics of the patients with or without restenosis after implantation of coronary stents.

|  | No restenosis (n = 168) | With restenosis (n = 116) | P |
|---|---|---|---|
| Extension of coronary artery disease |  |  | 0.79 |
| 1-vessel | 29.9% | 27.2% |  |
| 2-vessel | 42.1% | 41.2% |  |
| 3-vessel | 28% | 31.6% |  |
| Characteristics of the objective vessel |  |  | 0.21 |
| LAD | 45% | 44% |  |
| LCx | 26% | 26.3% |  |
| RCA | 29.5% | 29% |  |
| Left main | 0.5% | 0.7% |  |
| Lesion site |  |  | 0.73 |
| Ostial | 8% | 5% |  |
| Proximal | 40% | 46% |  |
| Midvessel | 46% | 44.5% |  |
| Distal | 6% | 4.5% |  |
| Lesion type |  |  | 0.48 |
| A | 12% | 13% |  |
| B1 | 24% | 22% |  |
| B2 | 36% | 36% |  |
| C | 28% | 29% |  |
| Diameter of stenosis, % |  |  |  |
| Baseline | 86 ± 10 | 86 ± 12 | 0.57 |
| Post-procedure | 1 ± 3 | 1 ± 3 | 0.39 |
| Follow-up | 25 ± 3.5 | 38 ± 3.5 | <0.001 |

TABLE 2-continued

Angiographic characteristics of the patients with or without restenosis after implantation of coronary stents.

|  | No restenosis (n = 168) | With restenosis (n = 116) | P |
|---|---|---|---|
| Reference vessel diameter, mm |  |  |  |
| Baseline | 3.20 ± 0.58 | 3.20 ± 0.51 | 0.79 |
| Post-procedure | 3.34 ± 0.558 | 3.32 ± 0.58 | 0.82 |
| Follow-up | 3.31 ± 0.47 | 3.24 ± 0.46 | 0.08 |
| Minimal luminal diameter, mm |  |  |  |
| Baseline | 0.48 ± 0.37 | 0.45 ± 0.37 | 0.35 |
| Post-procedure | 3.32 ± 0.56 | 3.31 ± 0.54 | 0.80 |
| Follow-up | 3.01 ± 0.70 | 0.88 ± 0.95 | <0.001 |
| Acute gain, mm | 2.91 ± 0.55 | 2.93 ± 0.61 | 0.74 |
| Late loss, mm | 0.67 ± 0.07 | 0.97 ± 0.14 | <0.001 |
| Loss index | 0.13 ± 0.23 | 0.88 ± 0.34 | <0.001 |
| Lesion length, mm | 18.6 ± 9.8 | 17.3 ± 9.0 | 0.26 |

LAD = left anterior descending artery;
LCx = left circumflex artery;
RCA = right coronary artery.

The present study analyzed 47 SNPS localized in 8 human genes regulating the cell cycle, including proliferation activators (cyclins A1, E1, B1, and D1) (See FIG. 1) and cell growth suppressors (p21, p27, p57, and p53) (See FIG. 2).

FIG. 1 shows the 25 SNPs examined in cell cycle activator genes and the protein they encode between brackets: CCNA1 (Cyclin A1), CCNE1 (Cyclin E1), CCNB1 (Cyclin B1) and CCND1 (Cyclin D1). The "Polymorphism" column includes position and the alleles associated to said polymorphisms. The position of the polymorphism is shown with respect to the start of the gene transcription, identified as the nucleotide base +1. The polymorphism is specified with a negative number when it is found before the start of transcription and with a positive number when it is localized in a posterior position. The "Localization" column represents the situation of the polymorphism with respect to the functional structure of the gene. In greater detail, the "Promoter region" localization specifies that the polymorphism is localized in the region regulating the transcription of the gene, which is localized before the start of transcription (indicated as +1). The "Exon" localization specifies that the polymorphism is localized in the coding region of the gene. The "Intron" localization specifies that the polymorphism is localized in a non-coding intronic region of the gene. The UTR 3' and UTR 5' localizations specify that the polymorphism is localized in a non-translated sequence in region 3' or 5', respectively.

FIG. 2 shows the 22 SNPs examined in cell cycle inhibitory genes and the protein they encode between brackets: CDKN1A (p21 Kip1/Cip1), CDKN1B (p27 Kip1/Cip1), CDKN1C (p57 Kip1/Cip1) and TP53 (p53).

The genotyping of the 47 SNPs (described below) was carried out in samples of DNA purified from circulating leukocytes of 284 patients subjected to revascularization by implantation of stents, of which 168 were not affected by restenosis and 116 suffered this disease (defining restenosis as a reduction in the internal diameter of the lumen of the vessel over 50% with respect to the lumen of the segment immediately adjacent to the intervened area after angiographic evaluation carried out in the period of 6 to 9 months after the intervention). The statistical analysis to identify those polymorphisms that could increase the risk of developing restenosis was carried out by logistic regression using the SNPStat programme (Sole, Guino, Valls, Iniesta and Moreno, "SNPStats: a web tool for the analysis of association studies" *Bioinformatics* 2006, 22, 1928-9). From the total of 47 SNPs analyzed, statistically significant association with greater risk of restenosis was only observed for SNPs 1-4, rs164390, rs350099, rs350104, rs875459, in the CCNB1 gene; SNP5, rs2282411, in the CCNA1 gene and SNP6, rs733590, in the CDKN1A gene.

FIG. 3 summarises the six SNPs that showed statistically significant association with the risk of developing restenosis after stent implantation.

FIG. 4 shows the results of the logistic regression analysis of the SNPs associated with risk of restenosis after the implantation of a stent. Analysis was performed using the SNPStat software (Sole, Guino, Valls, Iniesta and Moreno, "SNPStats: a web tool for the analysis of association studies", *Bioinformatics* 2006, 22, 1928-9), with correction by age and sex.

The results showed that, with respect to SNP1, the individuals carrying the T allele in homozygosis (T/T) have a significant 1.74-fold increase in the probability of developing restenosis with respect to the individuals carrying the C allele in homozygosis (C/C) or heterozygosis (C/T) (See FIG. 4).

With respect to SNP2, the individuals carrying the C allele in homozygosis (C/C) have a significant 1.77-fold increase in the probability of developing restenosis with respect to the individuals carrying the T allele in homozygosis (T/T) or heterozygosis (T/C) (See FIG. 4).

With respect to SNP3, the individuals carrying the G allele in homozygosis (G/G) have a significant 1.81-fold increase in the probability of developing restenosis with respect to the individuals carrying the T allele in homozygosis (T/T) or heterozygosis (G/T) (See FIG. 4).

In relation to SNP4, the individuals carrying the G allele in homozygosis (G/G) have a significant 1.78-fold increase in the probability of developing restenosis with respect to the individuals carrying the T allele in homozygosis (T/T) or heterozygosis (G/T). The logistic regression analysis applied to SNP4 took into consideration the following factors: restenosis, sex, age and family history of the analyzed patients (See FIG. 4).

With respect to SNP5, in a codominance model, the presence of the T allele in homozygosis (T/T) or in heterozygosis (C/T) with respect to the C allele in homozygosis (C/C) has a significant 1.26- and 3.10-fold increase in the probability of developing restenosis, respectively. In a dominance model, the presence of the G allele in homozygosis (G/G) is associated with a significant 1.78-fold increase in the probability of developing restenosis with respect to the T allele in homozygosis (T/T) or heterozygosis (G/T). The logistic regression analysis applied to SNP5 took into consideration the following factors: restenosis, sex, age and type of stents implanted in the analyzed patients (See FIG. 4).

In relation to SNP6, in a codominance model, the presence of the T allele in homozygosis (T/T) with respect to the C allele in heterozygosis (C/T) or in homozygosis (C/C) has a significant 1.92- and 2.38-fold increase in the probability of developing restenosis, respectively. In a dominance model, the presence of the T allele in homozygosis (T/T) has a significant 2.08-fold increase in the probability of developing restenosis with respect to the C allele in heterozygosis (T/C) or homozygosis (C/C) (See FIG. 4).

Gene Analysis

For the detection of the polymorphisms and the genotyping of the samples the LightCycler 480 Scanning software and the LightCycler 480 High Resolution Melting Master kit were used.

The mixture of the kit contained the fluorophore LightCycler 480 ResoLight, which homogeneously binds to the double strand of DNA and can be used in high concentrations without inhibiting the amplification reaction thanks to its chemical characteristics.

During the PCR reaction cycles, the formation of the amplified fragments was monitored. The samples with variations in their sequence were distinguished by discrepancies in the melting curves. By using this technique it was possible to differentiate between homozygote and heterozygote samples and even between wild and mutant homozygotes.

Design of Primers

The design of each pair of primers, used in the PCR reaction per gene was carried out with the Primer 3 programme (Howard Hughes Medical Institute and National Institutes of Health, National Human Genome Research Institute (See table 3).

In the design of the primers (See table 3), the melting temperature was indicated around 62° C. and the size of the amplicons between 100-250 bps.

TABLE 3

Primers designed for the polymorphisms studied

| Gene | SNP | GenBank | | Primers | |
|---|---|---|---|---|---|
| CCNB1 | SNP1 | rs350099 | Sense | AATAACGATCCAAAGAAACCAAATG | (SEQ ID NO 7) |
| | | | Antisense | CCCATAGAGCAACGGTATAAGAGC | (SEQ ID NO 8) |
| CCNB1 | SNP2 | rs350104 | Sense | CCCCGTTGCTAATGTGTGA | (SEQ ID NO 9) |
| | | | Antisense | GACATTCTTTCATTTGATCGTTGC | (SEQ ID NO 10) |
| CCNB1 | SNP3 | rs164390 | Sense | CCAAAGTGCTGGGATTACAGG | (SEQ ID NO 11) |
| | | | Antisense | CAATTATTCATATGGTCAACCA-CAAAC | (SEQ ID NO 12) |
| CCNB1 | SNP4 | rs875459 | Sense | GAGGCTAGGCTGGCTCTTCTC | (SEQ ID NO 13) |
| | | | Antisense | CATGGCTTCCTCTTCACCAG | (SEQ ID NO 14) |
| CCNA1 | SNP5 | rs2282411 | Sense | GTATGCCGCGTGATTTCTAGG | (SEQ ID NO 15) |
| | | | Antisense | CTGTGGGAAGAAAACTGAAAAGG | (SEQ ID NO 16) |
| CDKN1A | SNP6 | rs733590 | Sense | CTGGGCAGAGATTTCCAGACTC | (SEQ ID NO 17) |
| | | | Antisense | AAAATTGCAGAGGATGGATTGTTC | (SEQ ID NO 18) |

Amplification Reaction

For the amplification reaction the High Resolution the LightCycler® 480 Master kit from Roche Applied Science was used. The 2× mixture contained FastStart Taq polymerase DNA and the fluorophore LightCycler 480 ResoLight in the reaction buffer without $MgCl_2$. This mixture is compatible with the DMSO addition to improve the amplification of sequences rich in GC.

The FastStart Taq polymerase DNA is a heat stable enzyme, chemically modified, that does not show activity at temperatures of up to 75° C. The enzyme is active only at high temperatures, where the primers cannot bind non-specifically to the sequence.

a. Reagents and Volumes.

Table 4 lists the reagents used in each amplification reaction, the initial and final concentrations and the required volumes.

TABLE 4

Reagents and volumes

| Reagent | [Initial conc] | [Final conc.] | Volume (μL) |
|---|---|---|---|
| Master Mix | 2X | 1X | 5 |
| Primers | 4 μM | 0.2 μM | 0.5 |

TABLE 4-continued

Reagents and volumes

| Reagent | [Initial conc] | [Final conc.] | Volume (μL) |
|---|---|---|---|
| $MgCl_2$ | 25 mM | 3 mM | 1.2 |
| Water | — | — | 2.3 |
| DNA | 20 ng/μL | 2 ng/μL | 1 |
| Total volume | | | 10 | b. Reaction Conditions.

Table 5 shows the conditions for the amplification reaction after optimization of different parameters.

TABLE 5

Conditions for the amplification reaction

Setup

| Detection Format | HRM Dye |
|---|---|

Programs

| Program Name | Cycles | Analysis Mode |
|---|---|---|
| Pre-Denaturation | 1 | None |
| Amplification | 45 | Quantification |
| High Resolution Melting | 1 | Melting Curves |
| Cooling | 1 | None |

Temperature Targets

| Target [° C.] | Acquisition Mode | Hold (hh:mm:ss) | Ramp Rate (° C./s) (96-well/384-well) | Acquisitions (per ° C.) |
|---|---|---|---|---|
| Pre-Incubation | | | | |
| 95 | None | 00:10:00 | 4.8 | — |
| Amplification | | | | |
| 95 | None | 00:00:10 | 4.8 | — |
| 62 | None | 00:00:10 | 2.5 | — |
| 72 | Single | 00:00:10- | 4.8 | |

TABLE 5-continued

Conditions for the amplification reaction

00:00:20³⁾
High Resolution Melting

| 95 | None | 00:01:00 | 4.8 | |
|----|------|----------|-----|----|
| 40 | None | 00:01:00 | 2.5 | |
| 60 | None | 00:00:01 | 1 | |
| 95 | Continuous | — | — | 25 |

Cooling

| 40 | None | 00:00:10 | 4.8 | — |

The estimated time of the test was 75 min for the PCR and 15 min for the denaturation curve (High Resolution Melting). The reaction can be carried out in a conventional thermocycler and the results analized in a LightCycler 480 system.

In the specific case of the polymorphisms SNP1, SNP3 and SNP4, a microlitre of a standard sample with wild homozygote genotype for each polymorphism was added to each well after the amplification reaction prior to the denaturation step. In this way, it is possible to clearly distinguish between the two homozygotes.

Analysis of the Results

The LightCycler® 480 Gene Scanning software was used to determine the heteroduplex structures in the samples by the analysis of the experimental data generated using the LightCycler® 480 High Resolution Melting system.

After the samples were amplified by PCR and denatured to obtain melting curves, the software analyzed them and grouped the samples with a similar melting curve.

Figure 12A:
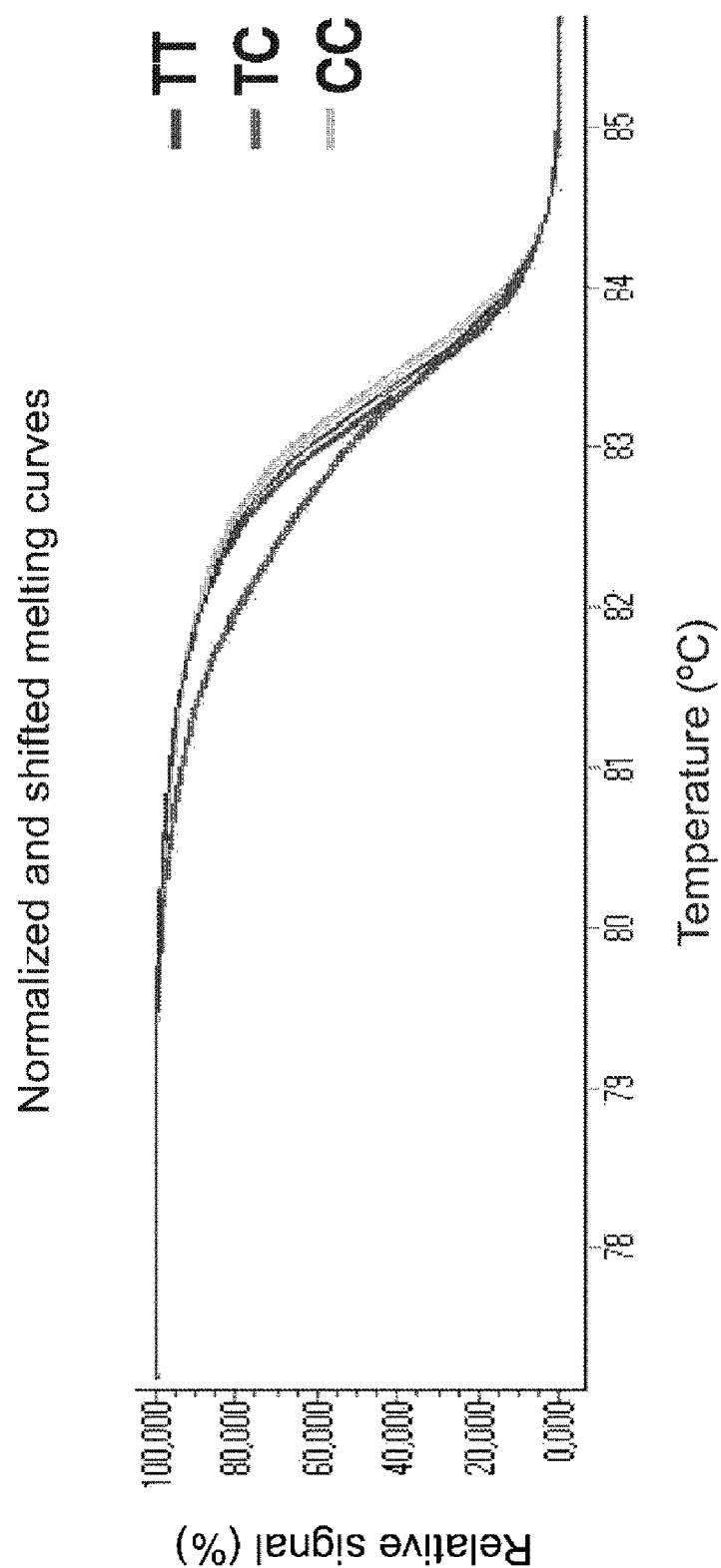
FIG. 12: Melting curves of SNP1. a) Representation of the curves that are normal and shifted by the presence of the polymorphism (depending on the temperature) b) Representation of the difference between normal curves and those shifted by the presence of the polymorphism (depending on the temperature). The differences in the melting curves are a result of the differences between variations in the sequence of the PCR products, grouping the samples depending on each genotype.
Figure 12B:
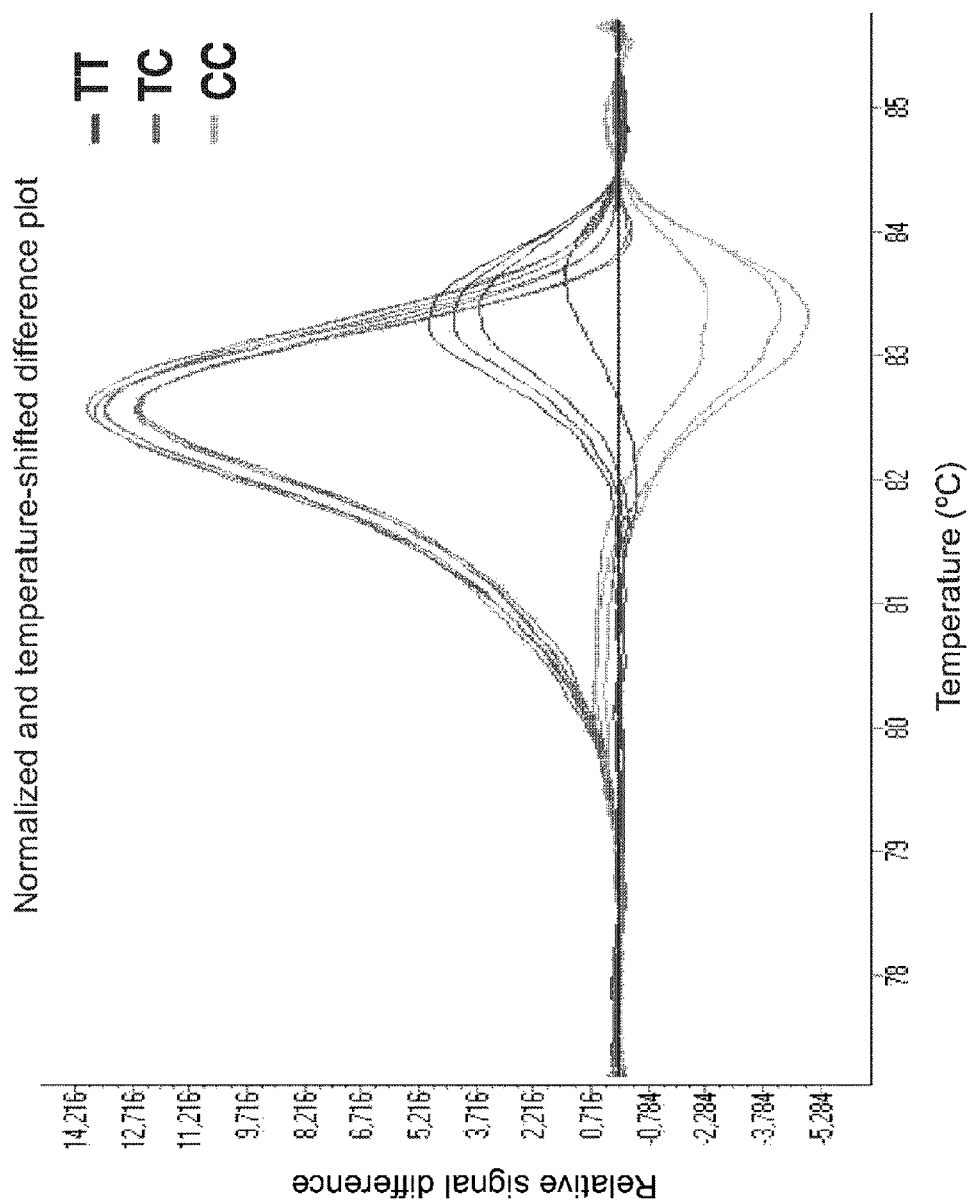
Figure 13A:
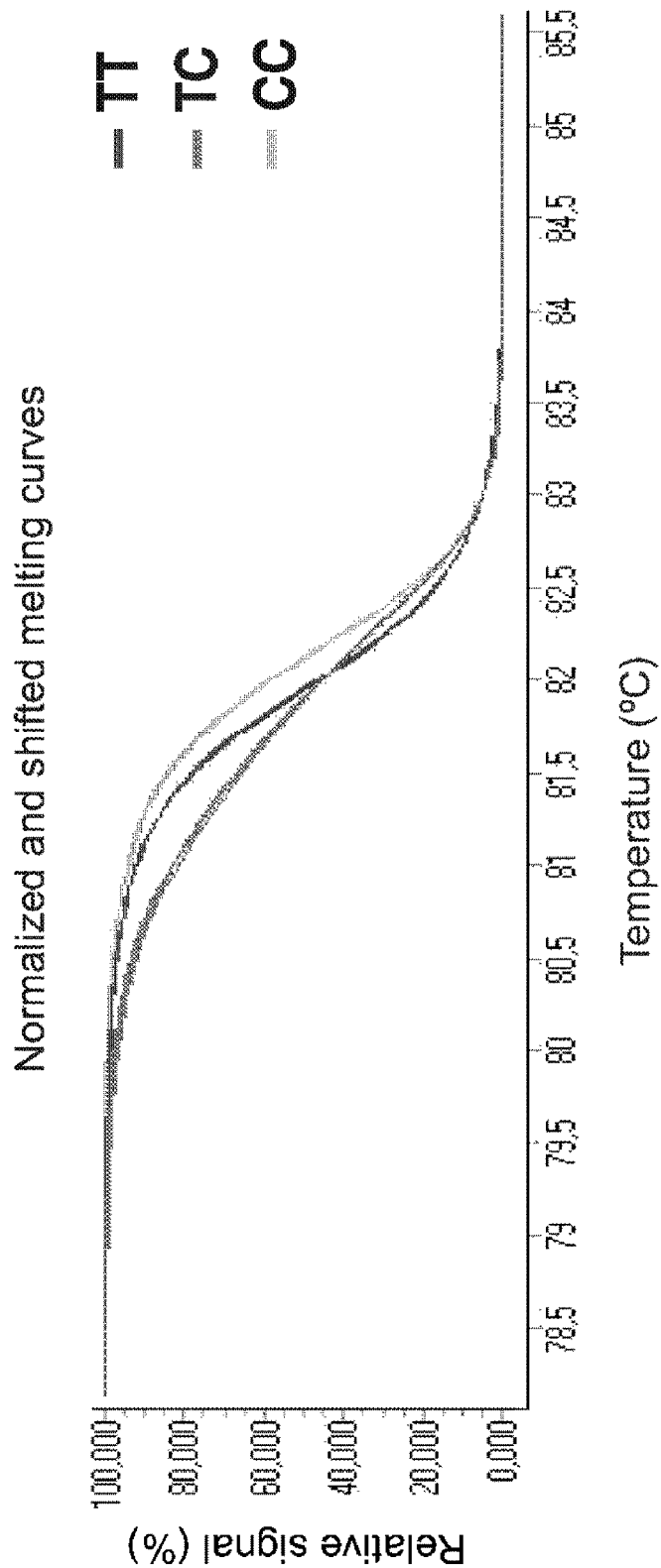
FIG. 13: Melting curves of SNP2. a) Representation of the curves that are normal and shifted by the presence of the polymorphism (depending on the temperature). b) Representation of the difference between normal curves and those shifted by the presence of the polymorphism (depending on the temperature). The differences in the melting curves are a result of the differences between variations in the sequence of the PCR products, grouping the samples depending on each genotype.
Figure 13B:
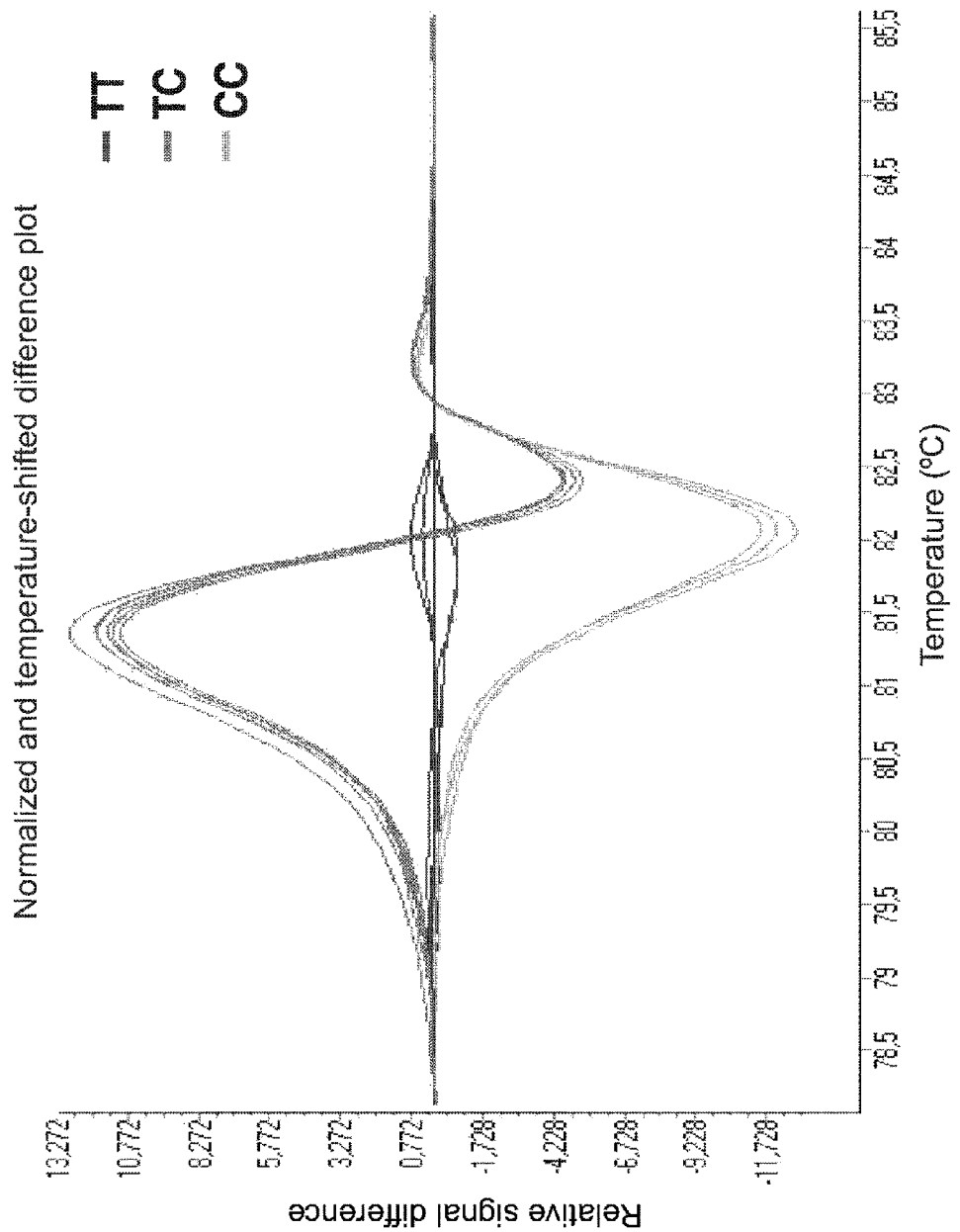
Figure 14A:
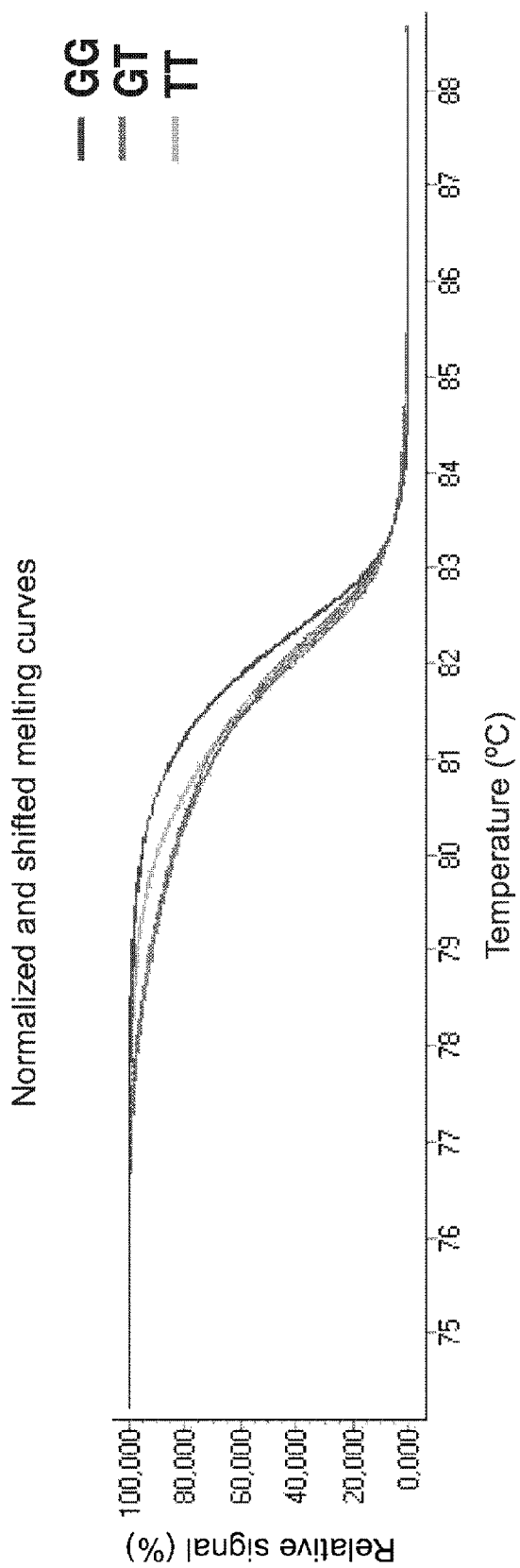
FIG. 14: Melting curves of SNP3. a) Representation of the curves that are normal and shifted by the presence of the polymorphism (depending on the temperature). b) Representation of the difference between normal curves and those shifted by the presence of the polymorphism (depending on the temperature). The differences in the melting curves are a result of the differences between variations in the sequence of the PCR products, grouping the samples depending on each genotype.
Figure 14B:
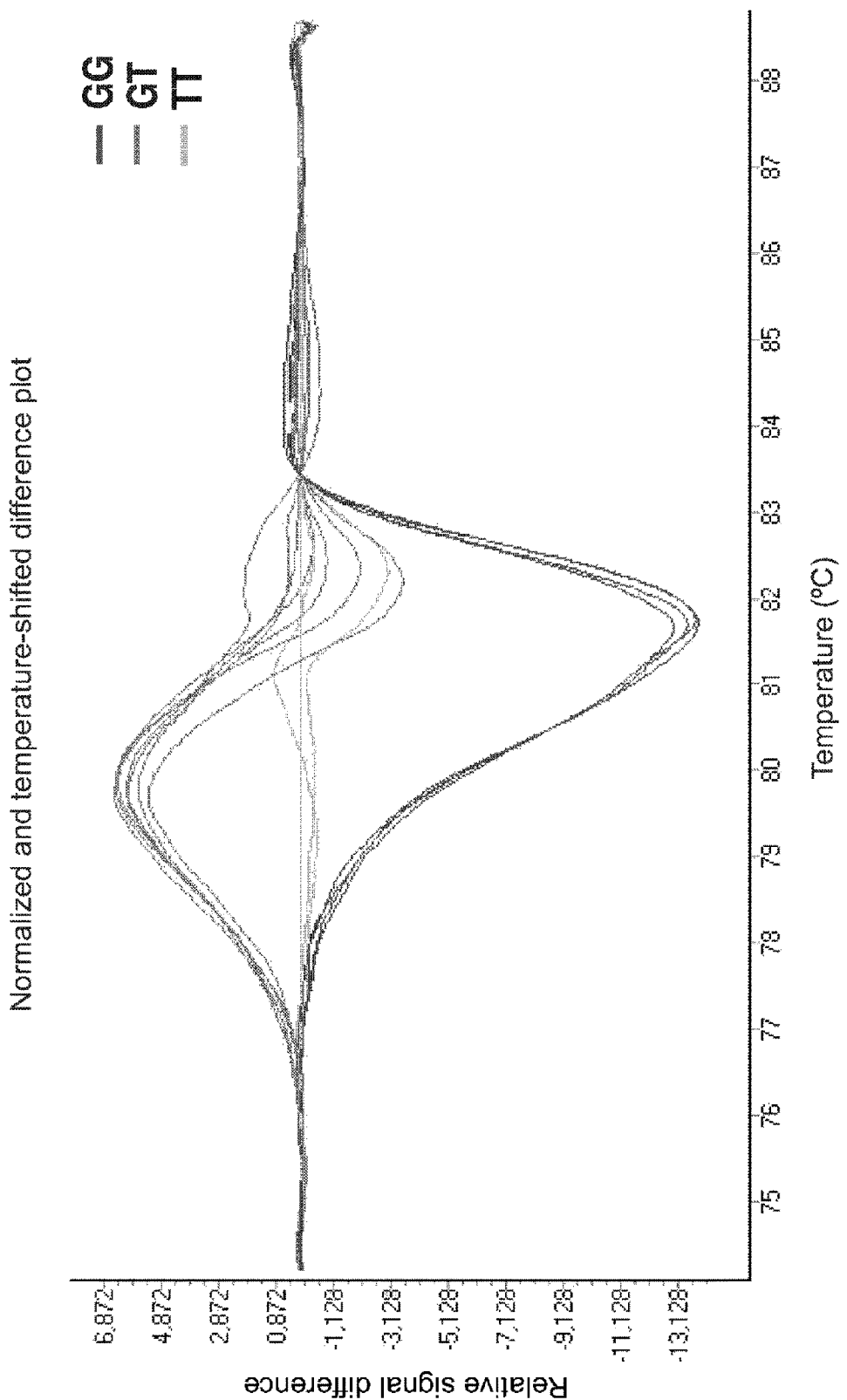
Figure 15A:
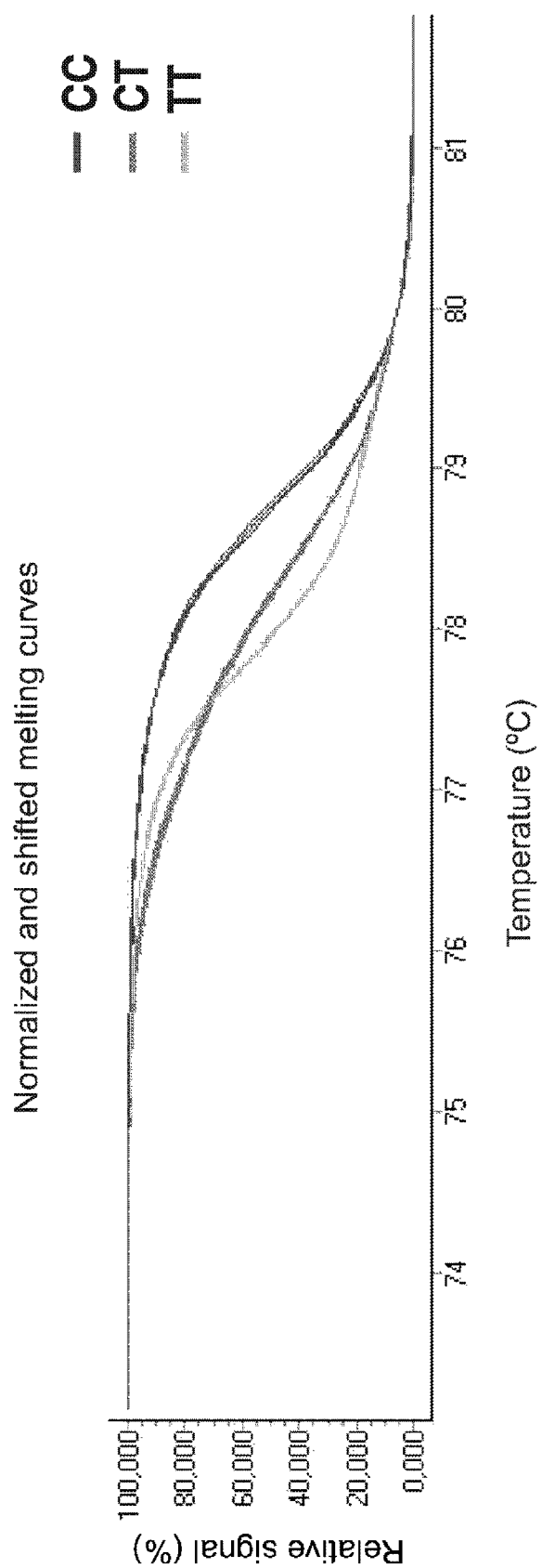
FIG. 15: Meting curves of SNP4. a) Representation of the curves that are normal and shifted by the presence of the polymorphism (depending on the temperature). b) Representation of the difference between normal curves and those shifted by the presence of the polymorphism (depending on the temperature). The differences in the melting curves are a result of the differences between variations in the sequence of the PCR products, grouping the samples depending on each genotype.
Figure 15B:
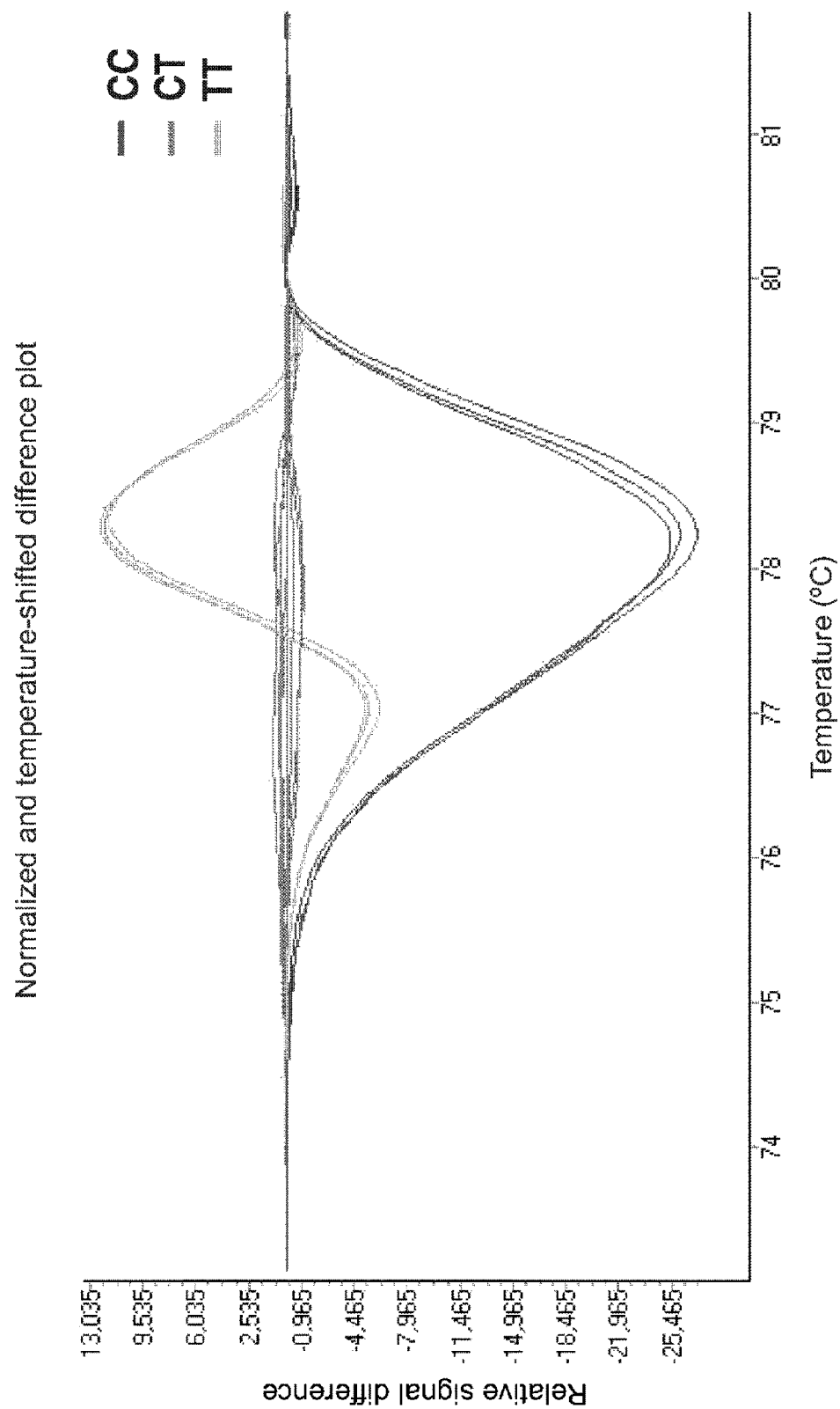
Figure 16A:
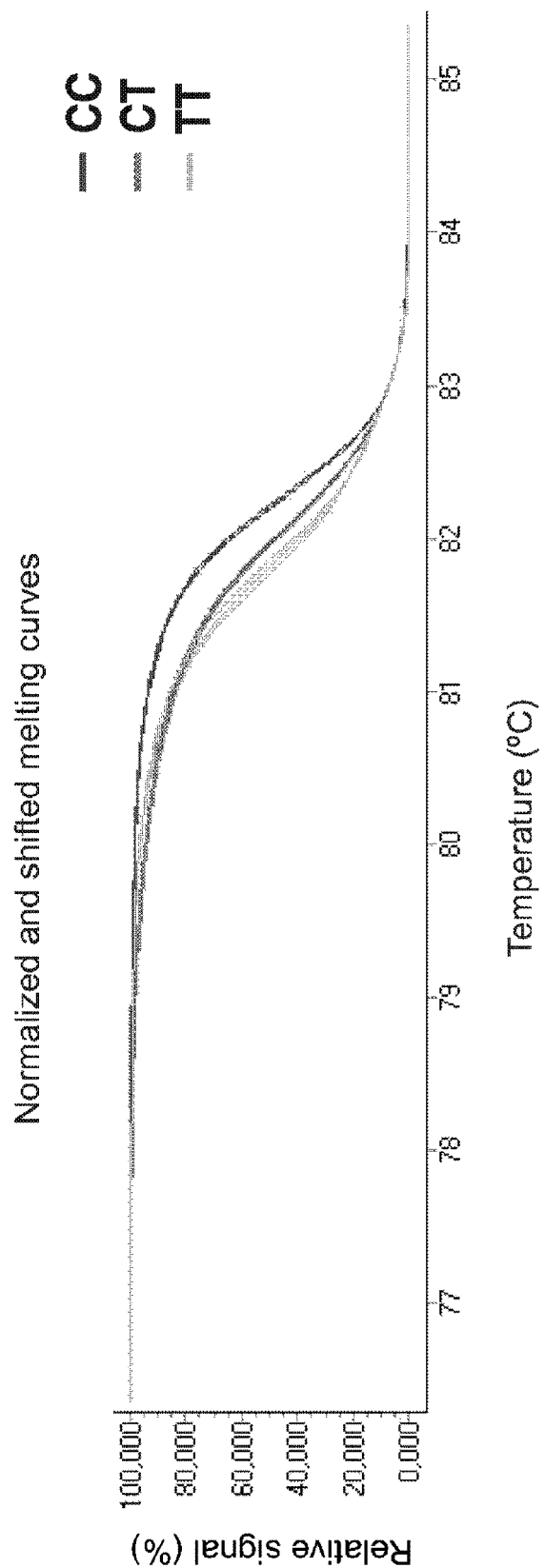
FIG. 16: Melting curves of SNP5. a) Representation of the curves that are normal and shifted by the presence of the polymorphism (depending on the temperature). b) Representation of the difference between normal curves and those shifted by the presence of the polymorphism (depending on the temperature). The differences in the melting curves are a result of the differences between variations in the sequence of the PCR products, grouping the samples depending on each genotype.
Figure 16B:
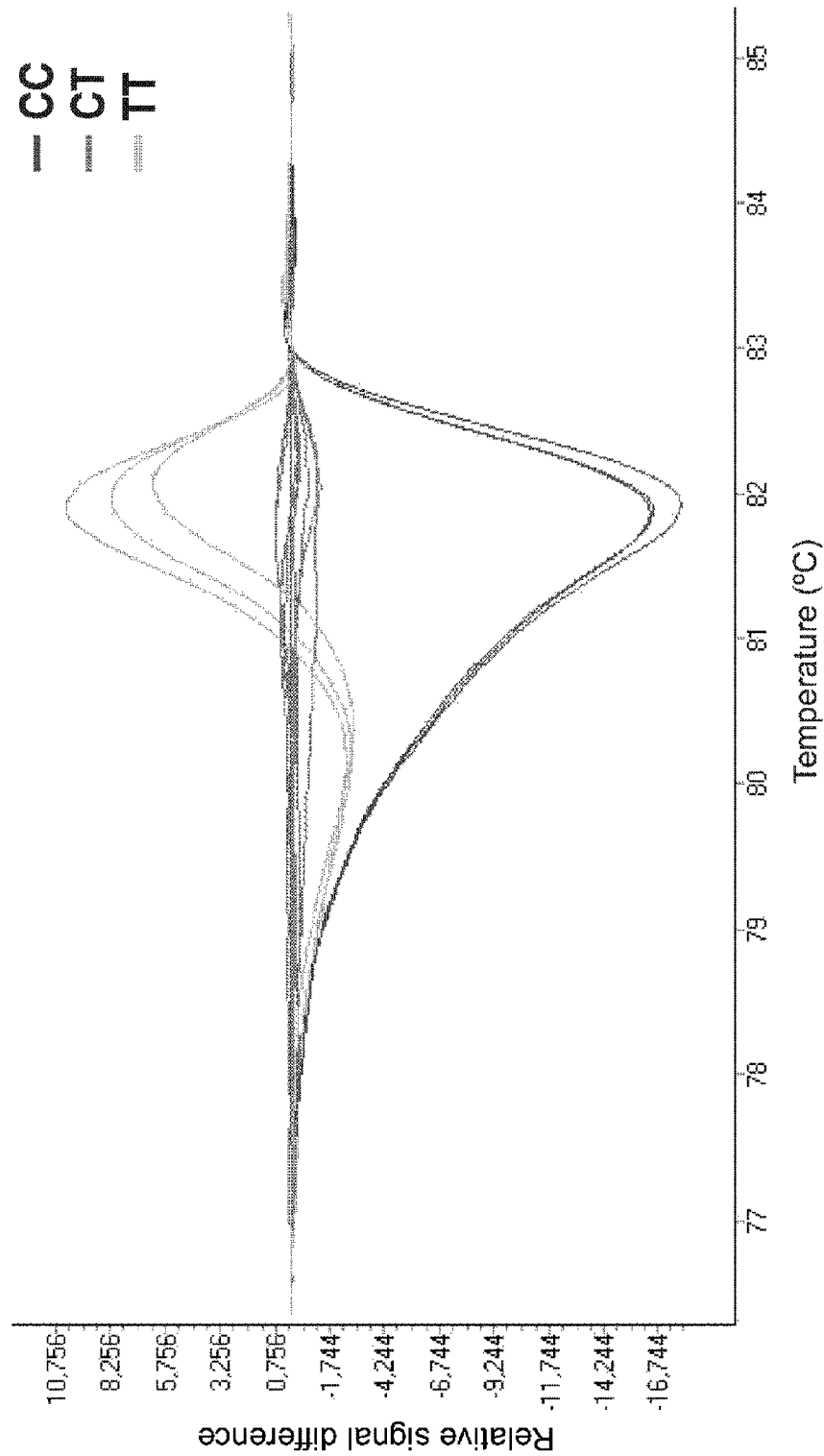

In FIGS. 12 and 13 the melting curves of SNP1 and SNP2 are shown, respectively. The two fragments of the CCNB1 gene that contained both polymorphisms were amplified in different samples of human genomic DNA using the "LightCycler 480 High Resolution Melting Mastee" kit and analyzed by the "LightCycler 480 Scanning" software. This software detects differences in the melting curves, resulting from the differences between variations in the sequence of the PCR products and grouping the samples depending on each genotype. In both figures each genotype is clearly distinguished, especially the homozygote variants (red and green). In panels (a) we can see the representation of the curves that are normal and altered by the presence of the polymorphism (depending on the temperature) whilst panels (b) represent the difference between normal curves and those altered by the presence of the polymorphism (depending on the temperature).

Figure 17A:
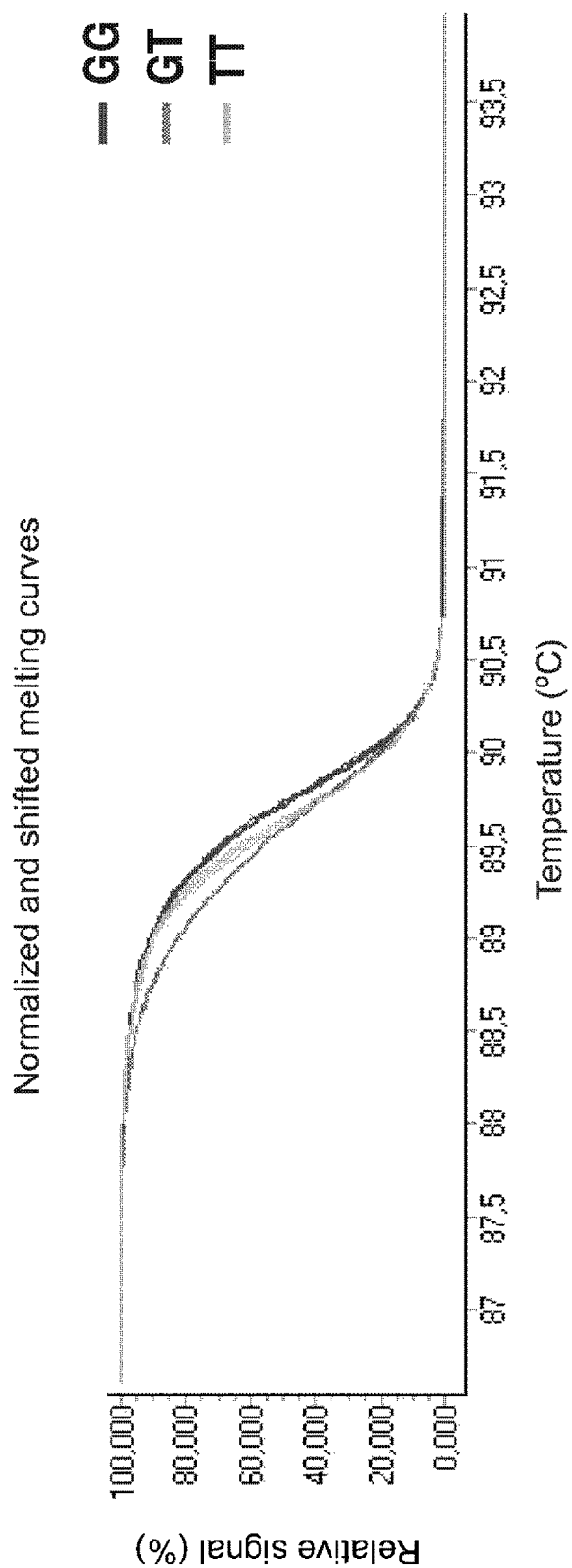
FIG. 17: Melting curves of SNP6. a) Representation of the curves that are normal and shifted by the presence of the polymorphism (depending on the temperature). b) Representation of the difference between normal curves and those shifted by the presence of the polymorphism (depending on the temperature). The differences in the melting curves are a result of the differences between variations in the sequence of the PCR products, grouping the samples depending on each genotype.
Figure 17B:
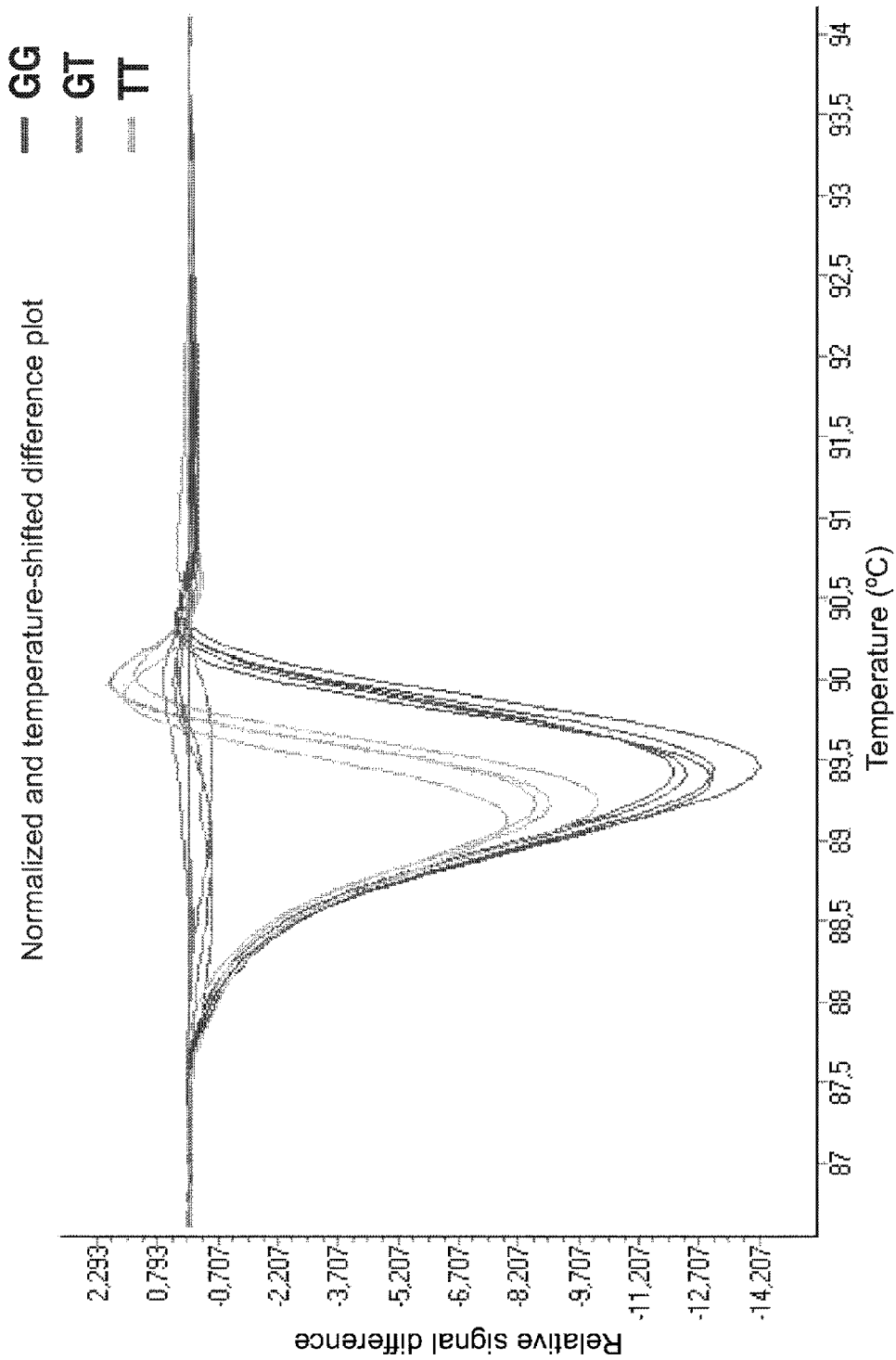

FIGS. 14, 15, 16 and 17 show the standardized melting curves, using the same methodology described in the previous paragraph, for the rest of the polymorphisms studied: the polymorphisms SNP3 (FIG. 14) and SNP4 (FIG. 15) of the CCNB1 gene, polymorphism SNP5 of the CCNA1 gene (FIG. 16) and SNP6 of the CDKN1A gene (FIG. 17).

Functional Studies Associated to Polymorphisms SNP1 and SNP2

Because the polymorphisms rs350099 (SNP1) and rs350104 (SNP2) are localized in the promoter region of the human CCNB1 gene, the inventors examined the possibility that the alleles of these polymorphisms that showed a statistically significant association with a greater risk of developing restenosis after implantation of stents could favour the binding of transcriptional activators and/or repressors that could in turn modify the gene's transcriptional activity.

The use of the Transfac® 7.0 database predicted the existence of NF-Y and AP-1 binding sites for the nucleotide sequences which contained the T and C alleles of the polymorphisms SNP1 and SNP2, respectively. These possibilities were tested using the EMSA technique.

Thus, the analysis of the sequence with the T allele of SNP1 predicted the existence of a CCAAT sequence with specificity for binding of the transcription factor NF-Y. However, the same type of analysis for the C allele of SNP1 did not predict said binding site.

Figure 7:
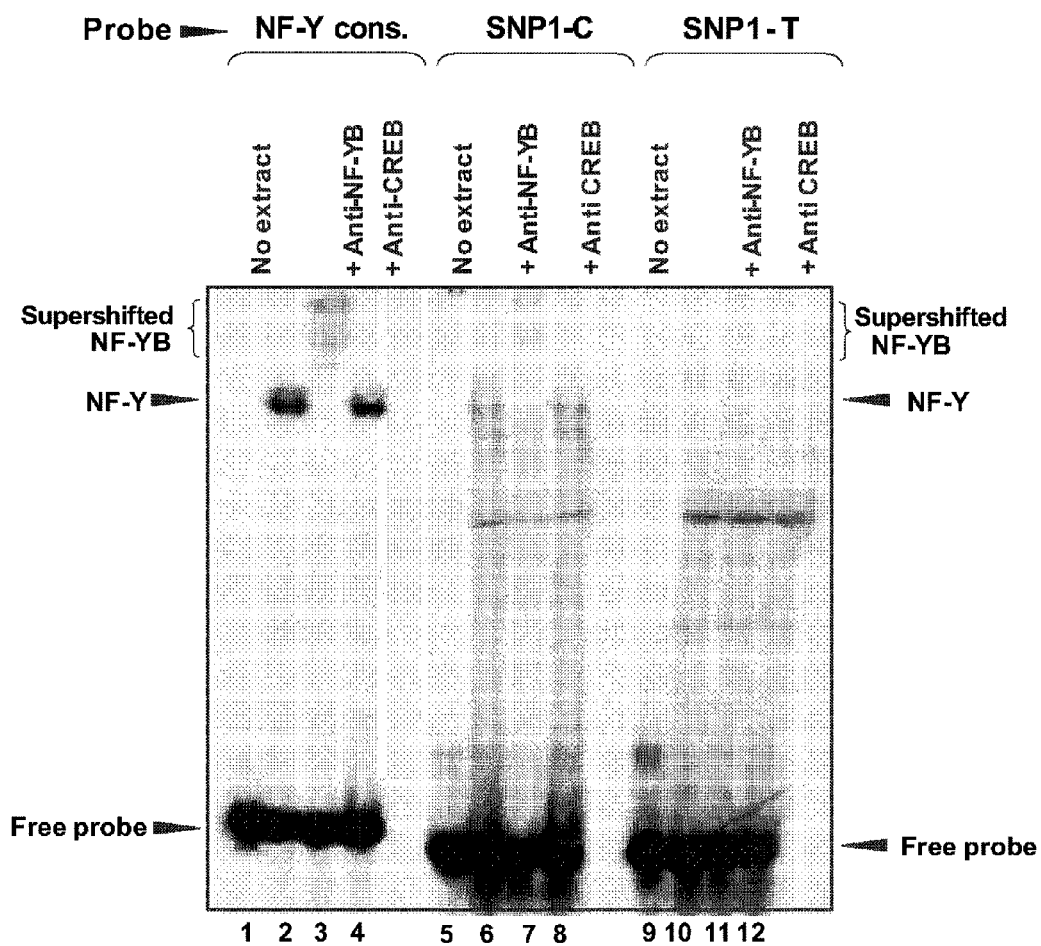
FIG. 7: EMSA resulting from incubation of the radiolabeled probes NF-Ycons, SNP1-T and SNP1-C with extracts from the soluble nuclear fraction of human cells derived from cervical cancer (HeLa). The supershift assays were performed by the incubation with the anti-NF-YB and anti-CREBII antibodies (this latter used as specificity control).
Figure 8:
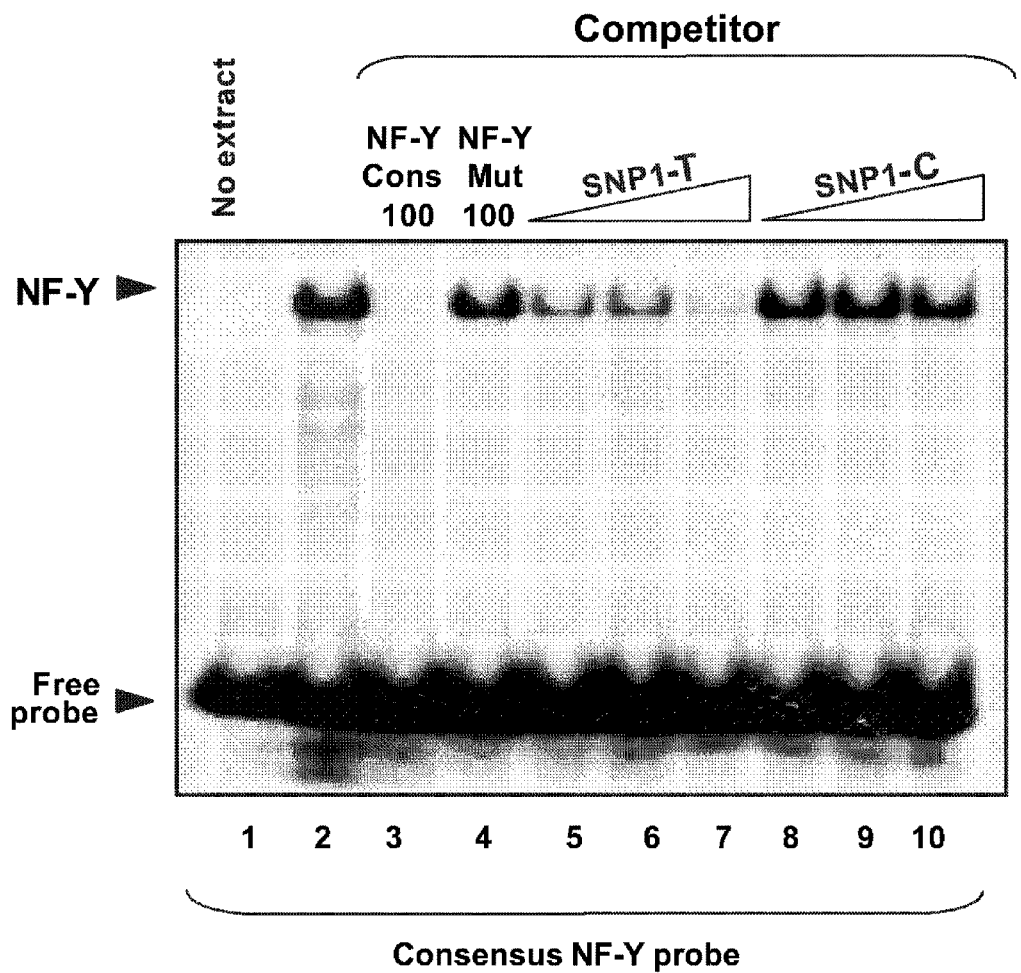
FIG. 8: Competition assay carried out by the EMSA technique resulting from the incubation of extracts of the soluble nuclear fraction of human cells derived from cervical cancer (HeLa) with radiolabeled NF-Ycons probe and an excess of unlabeled double-stranded oligonucleotides NF-Ycons, NF-Ymut, SNP1-T and SNP1-C.
Figure 9:
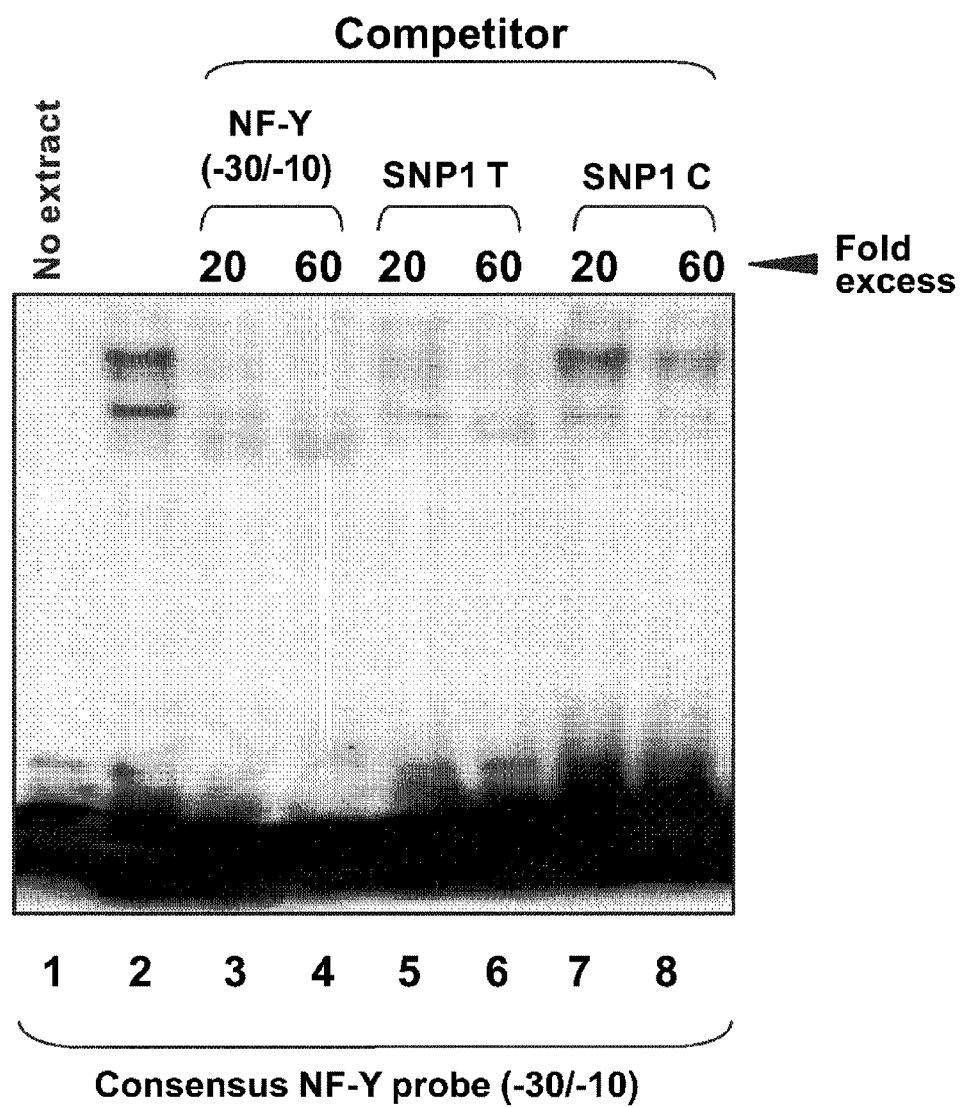
FIG. 9: Competition assay carried out by the EMSA technique resulting from the incubation of extracts of the soluble nuclear fraction of human cells derived from cervical cancer (HeLa) with radiolabeled NF-Y probe (−30/−10) and an excess of unlabeled double-stranded oligonucleotides NF-Y (−30/−10), SNP1-T and SNP1-C.

In accordance with these predictions, the data obtained in the study confirmed the efficient and specific binding of the NF-Y factor to the sequence containing the T allele with respect to the C allele in SNP1 (See FIGS. 7-9).

On the other hand, the analysis of the sequence with the C allele of SNP2 predicted the existence of an AP-1 binding site. However, the same type of analysis for the T allele of SNP2 did not predict such binding site. The data obtained in the study confirmed a greater AP-1 DNA-binding activity when the C allele is present in SNP2 with respect to the sequence which contains the T allele of the same polymorphism (See FIG. 10).

Electrophoretic Mobility Shift-Assay (EMSA)

The radioactive labelling of the probe was carried out by incubating 1 pmol of the double-stranded oligonucleotides at 65° C. for 10 min in a final volume of 10 µL to destabilize possible secondary structures. It was then quickly cooled in ice and 1 µL of T4-polinucleotide kinase and 1 µL of [γ³²P]-dATP (10 mCi/mL) were added. The labelling reaction was incubated at 37° C. for 30 min. The reaction was stopped in ice, the probe was purified in a Sephadex G-50 column and finally it was brought to a final volume of 100 µL.

FIG. 6 shows the detailed list of the double strand oligonucleotides used as probes for the EMSA assays. The "Sequence" column shows the sequences of the two complementary strands of each probe. The detailed description of the sequence contained in the probe is shown in the "Description" column. The predicted and consensus binding sequences to NF-Y and AP-1 are highlighted in bold and the alleles of SNPs are shown contained in the white boxes.

The protein of the soluble nuclear fraction of human cells (3 µg) was preincubated in a final volume of 17 µL of EMSA buffer (20 mM Tris-HCl pH: 7.8, 5% glycerol, 3 mM MgCl2, KCl 60 mM, 0.5 mM EDTA, 0.1 mM DTT, 50 µg/mL of poly(d(I-C)) for 10 min in ice. Next, 1 µl of radiolabeled double-stranded oligonucleotide probe was added and incubated for 30 min in ice. Finally, 1 µl of loading buffer was added to each tube and the samples were separated by electrophoresis in 5% native polyacrylamide gels. The separation is carried out for approximately 2 hours at 200 mV in TBE 0.5× buffer (prepared from a 5× stock) in a 5% polyacrylamide gel (80:1, acrylamide: bisacrylamide) prepared in TBE 0.5× buffer. The gels were vacuum dried with a temperature of 80° C. for 2 hours and they were analyzed by autoradiography (See FIGS. 7-10). For the competition assays, an excess of unlabeled double-stranded oligonucleotides was added during the preincubation step prior to the addition of radiolabeled probe. For supershift assays, 2 µg of specific antibody (anti-NF-YB *Santacruz Biotechnology, reference sc*-13045x) or non-specific antibody (anti-CREB-II, Santa Cruz Biotechnology, reference sc-180x) were incubated for 30' with nuclear extract prior to the addition of radiolabeled probe.

FIG. 7 shows the identification of NF-Y activity associated to the SNP1-T probe (polymorphic variant with the T allele of SNP1) but not in the SNP1-C probe (polymorphic variant with the C allele of SNP1), in HeLa cells using an EMSA assay. The assay was carried out by the incubation of 10 fmoles of the probes, NF-Ycons, SNP1-T and SNP1-C radioactively marked, and extracts of the soluble nuclear fraction of HeLa cells (3 µg, 12 µg and 12 µg of protein, respectively).

The samples were separated in polyacrylamide gel and the DNA-protein complexes were visualized by autoradiography. The binding reaction controls were incubated in the absence of nuclear extract (Lanes 1, 5 and 9). The supershift assays were performed with preincubation for 30 minutes with the anti-NF-YB and anti-CREB-Il antibodies (the latter used as specificity control).

FIG. 8 shows how an excess of SNP1-T probe, but not SNP1-C competes the DNA binding activity associated to the NF-Y sequence of the NF-Ycons probe. The competition assay was carried out using the EMSA technique carried out by the incubation of 10 fmoles of the NF-Ycons radiolabeled probe with 3 μg of protein extract of the soluble nuclear fraction of HeLa cells and an excess of the probes not radioactively marked ("cold" probe). The unlabeled double-stranded oligonucleotides used in the competition assays are (the excess is shown between brackets): NF-Ycons (Lane. 3: 100×), NF-Ymut (Lane. 4: 100×), SNP1-T (Lane. 5: 100×; Lane. 6: 300×; Lane. 7: 900×), and SNP1-T (Lane. 8: 100×; Lane. 9: 300×; Lane. 10: 900×). The samples were separated in polyacrylamide gel and the DNA-protein complexes were viewed by autoradiography.

FIG. 9 shows how an excess of SNP1-T probe, but not of SNP1-C competes the DNA binding activity associated to the NF-Y sequence of the −30/−10 region of the human gene promoter CCNB1. In greater detail, it shows the analysis of the binding sequence activity to NF-Y of the −27/−17 region of the CCNB1 promoter (NF-Y probe (−30/−10) competed with an excess of the "cold" probes SNP1-T and SNP1-C. The competition study was carried out by the EMSA technique incubating 10 fmoles of the NF-Y probe (−30/−10) radioactively marked, 8 μg of protein extract of the soluble nuclear fraction of HeLa cells and an excess of the "cold" probes NF-Y (−30/−10) (Lane 3: 20×; Lane 4: 60×), SNP1-T (Lane 5: 20×; Lane 6: 60×), and SNP1-C (Lane 7: 20×; Lane 8: 60×). The samples were separated in polyacrylamide gel and the DNA-protein complexes were viewed by autoradiography.

Figure 10A:
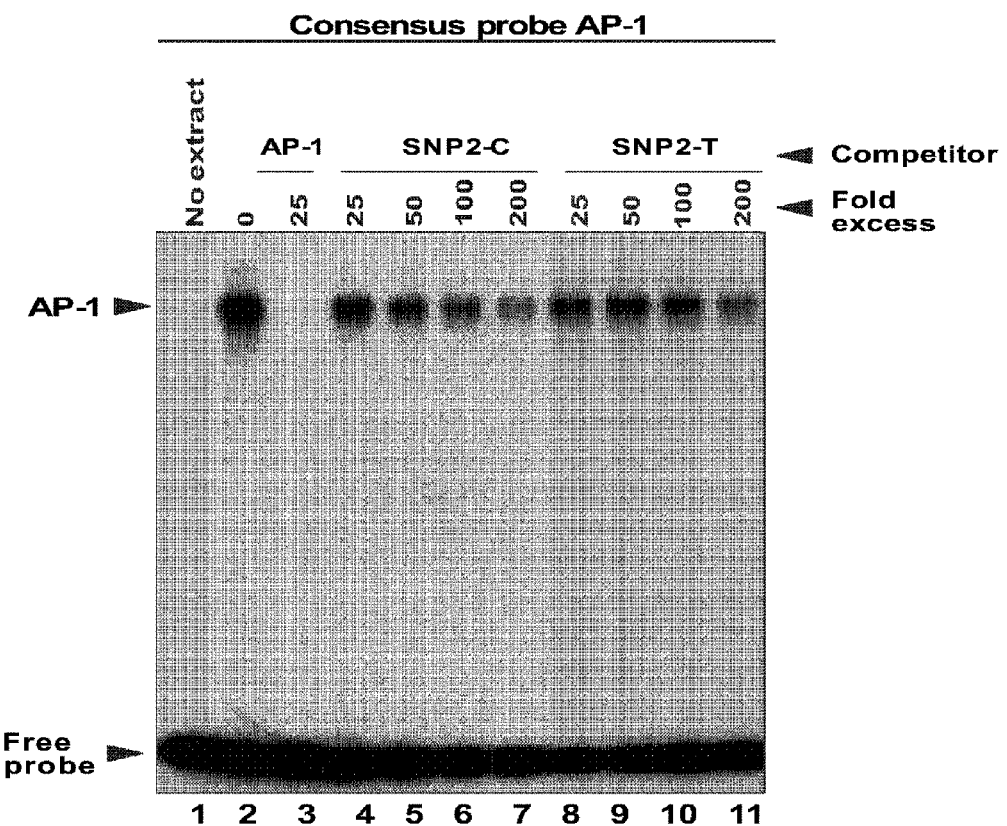
FIG. 10: a) Competition assay carried out by the EMSA technique resulting from the incubation of extracts of the soluble nuclear fraction of Human Bone Osteosarcoma Epithelial Cells (U2OS) with radiolabeled AP-1cons probe and an excess of unlabeled double-stranded oligonucleotides AP-1cons, SNP2-C and SNP2-T. b) Relative intensities of the DNA-protein complexes of an average of five EMSAs and the statistical analysis by one-way ANOVA and Bonferroni post-hoc test. The comparisons of band intensity in assay with competitor versus band intensity without competitor are represented as: *: $p<0.05$, **: $p<0.01$.
Figure 10B:
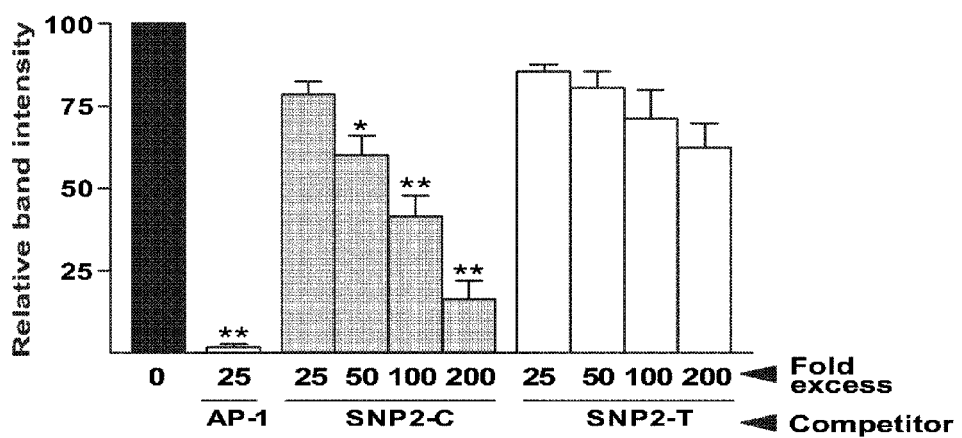

FIG. 10 shows how an excess of SNP2-C probe (polymorphic variant with the C allele of SNP2) competes more efficiently the DNA binding activity associated to the consensus AP-1 probe (AP-lcons), with respect to the SNP2-T probe (polymorphic variant with the T allele of SNP2). The assay was carried out by the EMSA technique incubating soluble nuclear extract of Human Bone Osteosarcoma Epithelial Cells (U2OS) and the radiolabeled AP-lcons probe. The competition experiments were performed by incubating a excess of the following unlabeled double-stranded oligonucleotides: AP-1 probe (25-fold excess, Lane 3), SNP2-C (25- to 200-fold, Lanes 4-7) and SNP2-T (25- to 200-fold, Lanes 8-11). The figure shows a representative EMSA from a total of five. The relative band intensity of the DNA-protein complexes in each EMSA was analyzed independently by a computerized image analysis system ("Metamorph software") and the values are represented in the graph as mean±SEM. The statistical analysis of the results was carried out by one-way ANOVA and Bonferroni post-hoc test. The comparisons with respect to the control (without competitor) are represented as: * $p<0.05$, ** $p<0.01$.

The invention claimed is:

1. Method for determining the risk of a human individual of developing restenosis after implantation of a stent which comprises: a) obtaining genomic DNA from a sample of said human individual; b) analyzing said sample to determine the genotype of at least one of the single-nucleotide polymorphisms (SNPs) selected from the group consisting of: rs350099, rs350104, rs164390 and rs875459, in the CCNB1 gene, c) identifying the presence of a genotype indicative of an increased risk of developing restenosis; wherein the presence of a genotype selected from the group consisting of: the presence of the TT genotype of rs350099 relative to a human individual that has a CC or CT genotype for this SNP, the presence of the CC genotype of rs350104 relative to a human individual that has a TT or TC genotype for this SNP, the presence of the GG genotype of rs164390 relative to a human individual that has a TT or GT genotype for this SNP and/or the presence of the GG genotype of rs875459 relative to a human individual that has a TT or GT genotype for this SNP, is indicative of an increased risk of developing restenosis; and d) determining the risk of said individual of developing restenosis after implantation of a stent.

2. A method according to claim 1, where the DNA sample is obtained from saliva, blood or leukocytes purified from blood.

3. A method according to claim 1, wherein step b) comprises determining the genotype of polymorphisms rs350099 and rs350104.

4. A method according to any of claim 1 or 3, which further comprises determining the genotype of the polymorphism rs2282411, of the CCNA1 gene, wherein the presence of the TT or TC genotype of rs2282411, in a codominance model, relative to a human individual that has a CC genotype, or the presence of the GG genotype, in a dominance model, relative to a human individual that has a TT or GT genotype, is indicative of an increased risk of developing restenosis.

5. A method according to any of claim 1 or 3, which further comprises determining the genotype of the polymorphism rs733590, of the CDKN1A gene, wherein the presence of the TT genotype of rs733590 relative to a human individual that has a CC or CT genotype, both in dominance and codominance models, is indicative of an increased risk of developing restenosis.

* * * * *

SEQUENCE LISTING

<160> NUMBER OF SEQ ID NOS: 34

<210> SEQ ID NO 1
<211> LENGTH: 52
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence of nucleotides adjacent to SNP1

<400> SEQUENCE: 1
tgacttccag cgccaggagt ctctatyggc tcttataccg ttgctctatg gg          52

<210> SEQ ID NO 2
<211> LENGTH: 52
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence of nucleotides adjacent to SNP2

<400> SEQUENCE: 2
tcagttcccc cgttgctaat gtgtgaycct ggcaaagtca tctaagtcgc tg          52

<210> SEQ ID NO 3
<211> LENGTH: 52
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence of nucleotides adjacent to SNP3

<400> SEQUENCE: 3

```
gcggaacggc tgttggtttc tgctggktgt aggtccttgg ctggtcgggc ct         52
```

<210> SEQ ID NO 4
<211> LENGTH: 52
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence of nucleotides adjacent to SNP4

<400> SEQUENCE: 4

```
catgtttgct ttatttcttg gtgatgktgt tgtttgtggt tgaccatatg aa         52
```

<210> SEQ ID NO 5
<211> LENGTH: 52
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence of nucleotides adjacent to SNP5

<400> SEQUENCE: 5

```
ggatgattgg gaaaggttga tttttaygct ccttggcact ggaagttcct ag         52
```

<210> SEQ ID NO 6
<211> LENGTH: 52
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence of nucleotides adjacent to SNP6

<400> SEQUENCE: 6

```
ctgctccaag cctgggttct gttttyagt gggatttctg ttcagatgaa ca         52
```

<210> SEQ ID NO 7
<211> LENGTH: 25
<212> TYPE: DNA
<213> ORGANISM: Artificial Sequence
<220> FEATURE:
<223> OTHER INFORMATION: sense primer SNP1

<400> SEQUENCE: 7

```
aataacgatc caaagaaacc aaatg                                      25
```

<210> SEQ ID NO 8
<211> LENGTH: 24
<212> TYPE: DNA
<213> ORGANISM: Artificial Sequence
<220> FEATURE:
<223> OTHER INFORMATION: antisense primer SNP1

<400> SEQUENCE: 8

```
cccatagagc aacggtataa gagc                                       24
```

<210> SEQ ID NO 9
<211> LENGTH: 19
<212> TYPE: DNA
<213> ORGANISM: Artificial Sequence
<220> FEATURE:
<223> OTHER INFORMATION: sense primer SNP2

<400> SEQUENCE: 9

```
ccccgttgct aatgtgtga                                             19
```

<210> SEQ ID NO 10
<211> LENGTH: 24
<212> TYPE: DNA
<213> ORGANISM: Artificial Sequence
<220> FEATURE:
<223> OTHER INFORMATION: antisense primer SNP2

<400> SEQUENCE: 10
gacattcttt catttgatcg ttgc                               24

<210> SEQ ID NO 11
<211> LENGTH: 21
<212> TYPE: DNA
<213> ORGANISM: Artificial Sequence
<220> FEATURE:
<223> OTHER INFORMATION: sense primer SNP3

<400> SEQUENCE: 11
ccaaagtgct gggattacag g                                  21

<210> SEQ ID NO 12
<211> LENGTH: 27
<212> TYPE: DNA
<213> ORGANISM: Artificial Sequence
<220> FEATURE:
<223> OTHER INFORMATION: antisense primer SNP3

<400> SEQUENCE: 12
caattattca tatggtcaac cacaaac                            27

<210> SEQ ID NO 13
<211> LENGTH: 21
<212> TYPE: DNA
<213> ORGANISM: Artificial Sequence
<220> FEATURE:
<223> OTHER INFORMATION: sense primer SNP4

<400> SEQUENCE: 13
gaggctaggc tggctcttct c                                  21

<210> SEQ ID NO 14
<211> LENGTH: 20
<212> TYPE: DNA
<213> ORGANISM: Artficial Sequence
<220> FEATURE:
<223> OTHER INFORMATION: antisense primer SNP4

<400> SEQUENCE: 14
catggcttcc tcttcaccag                                    20

<210> SEQ ID NO 15
<211> LENGTH: 21
<212> TYPE: DNA
<213> ORGANISM: Artificial Sequence
<220> FEATURE:
<223> OTHER INFORMATION: sense primer SNP5

<400> SEQUENCE: 15
gtatgccgcg tgatttctag g                                  21

<210> SEQ ID NO 16
<211> LENGTH: 23
<212> TYPE: DNA
<213> ORGANISM: Artificial Sequence
<220> FEATURE:
<223> OTHER INFORMATION: antisense primer SNP5

<400> SEQUENCE: 16
ctgtgggaag aaaactgaaa agg                                         23

<210> SEQ ID NO 17
<211> LENGTH: 22
<212> TYPE: DNA
<213> ORGANISM: Artificial Sequence
<220> FEATURE:
<223> OTHER INFORMATION: Sense primer SNP6

<400> SEQUENCE: 17
ctgggcagag atttccagac tc                                          22

<210> SEQ ID NO 18
<211> LENGTH: 24
<212> TYPE: DNA
<213> ORGANISM: Artificial Sequence
<220> FEATURE:
<223> OTHER INFORMATION: antisense primer SNP6

<400> SEQUENCE: 18
aaaattgcag aggatggatt gttc                                        24

<210> SEQ ID NO 19
<211> LENGTH: 23
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 5'-3' carrier of the T allele of
      SNP rs350099

<400> SEQUENCE: 19
gagtctctat tggctcttat acc                                         23

<210> SEQ ID NO 20
<211> LENGTH: 23
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 3'-5' carrier of the T allele of SNP
      rs350099

<400> SEQUENCE: 20
ctcagagata accgagaata tgg                                         23

<210> SEQ ID NO 21
<211> LENGTH: 23
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 5'-3' carrier of the C allele of SNP
      rs350099

<400> SEQUENCE: 21
gagtctctat cggctcttat acc                                         23

<210> SEQ ID NO 22
<211> LENGTH: 23
<212> TYPE: DNA
<213> ORGANISM: Homo sapiens
<220> FEATURE:

-continued

<221> NAME/KEY: misc_feature
<222> LOCATION: (0)...(0)
<223> OTHER INFORMATION: Sequence 3'-5' carrier of the C allele of SNP
      rs350099

<400> SEQUENCE: 22
ctcagagata gccgagaata tgg                                             23

<210> SEQ ID NO 23
<211> LENGTH: 27
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 5'-3' carrier of a NF-Y consensus
      binding site

<400> SEQUENCE: 23
ccgcagccgc caatgggaag ggagtga                                         27

<210> SEQ ID NO 24
<211> LENGTH: 27
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 3'-5' carrier of a NF-Y consensus
      binding site

<400> SEQUENCE: 24
ggcgtcggcg gttacccttc cctcact                                         27

<210> SEQ ID NO 25
<211> LENGTH: 27
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 5'-3' carrier of a mutated NF-Y site
      (CC/TT)

<400> SEQUENCE: 25
ccgcagccgt taatgggaag ggagtga                                         27

<210> SEQ ID NO 26
<211> LENGTH: 27
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 3'-5'carrier of a mutated NF-Y site
      (CC/TT)

<400> SEQUENCE: 26
ggcgtcggca attacccttc cctcact                                         27

<210> SEQ ID NO 27
<211> LENGTH: 21
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 5'-3' carrier of the T allele of SNP
      rs350104

```
<400> SEQUENCE: 27
taatgtgtga tcctggcaaa g                                              21

<210> SEQ ID NO 28
<211> LENGTH: 21
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 3'-5' carrier of the T allele of SNP
      rs350104

<400> SEQUENCE: 28
attacacact aggaccgttt c                                              21

<210> SEQ ID NO 29
<211> LENGTH: 21
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 5'-3' carrier of the C allele of SNP
      rs350104

<400> SEQUENCE: 29
taatgtgtga ccctggcaaa g                                              21

<210> SEQ ID NO 30
<211> LENGTH: 21
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 3'-5' carrier of the C allele of SNP
      rs350104

<400> SEQUENCE: 30
attacacact gggaccgttt c                                              21

<210> SEQ ID NO 31
<211> LENGTH: 21
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 5'-3' carrier of an AP-1 consensus
      binding site

<400> SEQUENCE: 31
cgcttgatga gtcagccgga a                                              21

<210> SEQ ID NO 32
<211> LENGTH: 21
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 3'-5' carrier of an AP-1 consensus
      binding site

<400> SEQUENCE: 32
gcgaactact cagtcggcct t                                              21
```

```
<210> SEQ ID NO 33
<211> LENGTH: 20
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 5'-3' carrier of a NF-Y binding
      site in the promoter region of the human CCNB1 gene

<400> SEQUENCE: 33
ggcagccgcc aatgggaagg                                               20

<210> SEQ ID NO 34
<211> LENGTH: 20
<212> TYPE: DNA
<213> ORGANISM: Homo sapiens
<220> FEATURE:
<221> NAME/KEY: misc_feature
<222> LOCATION: (0)...(0)
<223> OTHER INFORMATION: Sequence 3'-5'carrier of a NF-Y binding
      site in the promoter region of the human CCNB1 gene

<400> SEQUENCE: 34
ccgtcggcgg ttaccttcc                                                20
```